Figure 1:
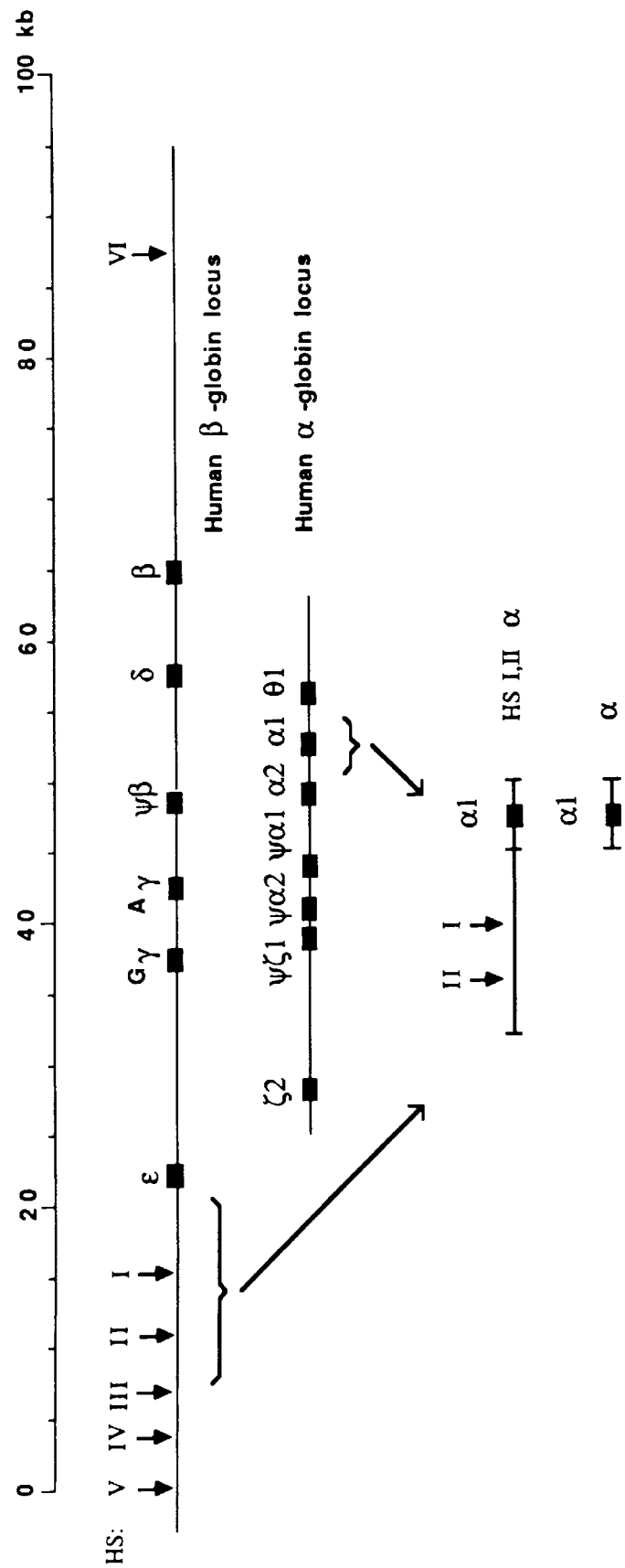

United States Patent [19]
Townes et al.

[11] Patent Number: 6,022,736
[45] Date of Patent: Feb. 8, 2000

[54] NUCLEIC ACID VECTORS COMPRISING DNASE I HYPERSENSITIVE SITES

[75] Inventors: Tim M. Townes; Thomas M. Ryan, both of Birmingham, Ala.; Richard D. Palmiter, Seattle, Wash.; Ralph L. Brinster, Gladwyne; Richard R. Behringer, Philadelphia, both of Pa.

[73] Assignees: The UAB Research Foundation, Birmingham, Ala.; The Trustees of the University of Pennsylvania, Philadelphia, Pa.; Board of Regents of the University of Washington, Seattle, Wash.

[21] Appl. No.: 08/471,483

[22] Filed: Jun. 6, 1995

Related U.S. Application Data

[62] Division of application No. 08/275,313, Jul. 13, 1994, Pat. No. 5,602,306, which is a continuation of application No. 07/923,007, Jul. 30, 1992, abandoned, which is a continuation of application No. 07/472,531, Jan. 30, 1990, abandoned, which is a continuation-in-part of application No. 07/412,977, Sep. 26, 1989, abandoned.

[51] Int. Cl.$^7$ .......................... C12N 15/63; C12N 15/09; C12N 15/00; C12N 5/00
[52] U.S. Cl. ..................... 435/320.1; 435/455; 435/69.1; 435/948; 800/13; 800/21; 800/5; 536/24.1
[58] Field of Search ............................ 435/320.1, 172.3, 435/948, 455, 69.1; 935/26, 27, 31, 32, 34; 536/24.1; 800/13, 21, 5

[56] References Cited

U.S. PATENT DOCUMENTS 5,532,143 7/1996 Grosveld et al. ..................... 435/69.1

FOREIGN PATENT DOCUMENTS

WO89/01517 2/1989 WIPO.

OTHER PUBLICATIONS

Hammer et al., Nature 315:680, 1985.
Palmiter and Brinster, Ann. Rev. Genet. 20:465, 1986.
Goring et al., Science 235:456–458, 1987.
Van Brunt, Biotechnology 6(10):1149, 1151, 1152, 1154, 1988.
Wilmut et al., New Scientist, pp. 56–59, 1988.
Novak et al., Proc. Natl. Acad. Sci. USA 87:3386, 1990.
Shih et al., Nucl. Acids Res. 18:4565, 1990.
Enver et al., Developmental Biol. 86:7033, 1989.
Watson et al., Molecular Biology of the Gene (4th ed.), pp. 650, 692–693, 1987.
Fritsch et al., Cell 19:959–72, 1980.
Wright et al., Nature 305:333–36, 1983.
Charnay et al., Cell 38:251–63, 1984.
Behringer, Proc. Natl. Acad. Sci. USA 84:7056–60, 1987.
Kollias et al., Nucl. Acids Res. 15:5739–47, 1987.
Hesse, Proc. Natl. Acad. Sci. USA 83:4312–16, 1986.
Choi et al., Nature 323:731–34, 1986.
Tuan, Proc. Natl. Acad. Sci. USA 82:6384–88, 1985.
Forrester et al., Proc. Natl. Acad. Sci. USA 83:1359–63, 1986.
Brinster et al., Proc. Natl. Acad. Sci. USA 82:4438–42, 1985.
Wagner et al., Proc. Natl. Acad. Sci. USA 78:6376–80, 1981.
McKnight et al., Cell 34:335–41, 1983.
Ritchie et al., Nature 312:517–20, 1984.
Goodhardt et al., Proc. Natl. Acad. Sci. USA 84:4229–33, 1987.
Stall et al., Proc. Natl. Acad. Sci. USA 85:3546–50, 1988.
Chamberlain et al., Proc. Natl. Acad. Sci. USA 85:7690–94, 1988.
Nishi, Nature 331:267–269, 1988.
Shani et al., Nature 314:283–6, 1985.
Small, Mol. Cell. Biol. 5:642–648, 1985.
Chisari, Science 230:1157–63, 1985.
Bucchini et al., Nature 326:409–11, 1987.
Krimpenfort et al., EMBO J. 6:1673–76, 1987.
Townes et al., EMBO J. 4:1715–23, 1985.
Spandidos et al., EMBO J. 1:15–20, 1982.
Chao et al., Cell 32:483–93, 1983.
Chada et al., Nature 314:377–80, 1985.
Magram et al., Nature 315:338–40, 1985.
Constantini et al., Cold Spring Harbor Symp. Quant. Biol. 50:361–70, 1985.
Kollias et al., Cell 46:89–94, 1986.
Treisman et al., Proc. Natl. Acad. Sci. USA 80:7428–32, 1983.
Banerji et al., Cell 27:299–308, 1981.
Green et al., Cell 35:137–48, 1983.
Martinell et al., Proc. Natl. Acad. Sci. USA 78:5056–60, 1981.

(List continued on next page.)

*Primary Examiner*—Brian R. Stanton
*Assistant Examiner*—Jill D. Martin
*Attorney, Agent, or Firm*—Clark & Elbing LLP

[57] ABSTRACT

The present invention provides novel recombinant nucleic acid vectors which may be used to produce α-globin as well as other proteins of interest in quantity in the red blood cells of transgenic animals or cell cultures of erythroid lineage. The present invention also provides for the transgenic animals which contain these recombinant nucleic acid vectors. The vectors of the invention comprise at least one of the major DNase I hypersensitivity sites associated with the β-globin locus together with a gene of interest. According to various embodiments of the invention, the vectors may be used to create transgenic animals or to transfect cells in culture. In a specific embodiment of the invention, a vector which comprises two DNase I hypersensitivity sites together with the human α-globin gene is used to create transgenic animals which produce human α-globin protein in erythroid tissues, including red blood cells. In a preferred specific embodiment of the invention, transgenic animals are created which comprise human α-globin and β-globin genes, each under the transcriptional influence of two β-globin locus DNase hypersensitivity sites; these transgenic animals express human hemoglobin in their erythroid tissues, and can be used to produce human hemoglobin in quantity.

33 Claims, 19 Drawing Sheets

OTHER PUBLICATIONS

Skow, Cell 34:1043–52, 1983.
Rubin et al., Am. J. Hum. Genet. 42:585–91, 1988.
Rubin et al., J. Clin. Invest. 82:1129–33, 1988.
Forrester et al., Nucl. Acid. Res. 15:10159–77, 1987.
Li et al., J. Biol. Chem. 260:14901–10, 1985.
Brinster et al., Nature 306:332–36, 1983.
Rexroad et al., J. Reprod. Fer. Supp. 41: 119–124, 1990.
Swanson et al., Biotechnology, 10:557–559, 1992.
D. Gross et al. Ann. Rev. Biochem. 57: 159–197 ('88).
Declaration & Form PCT/DO/EO/903 showing priority benefit of PCT/GB88/00655 filed Aug. 8, 1988 for Pat. #5532143.
P. Mellon et al. Cell ('81) 27(2 pt. 1) 279–88.
Behringer et al., Science 245: 971–973 (1989).
Ryan et al. (a), PNAS 86: 37–41 (1989).
Ryan et al. (b), Genes & Development 3: 314–323 (1989).
Talbot et al., Nature 338: 352–355 (1989).
van Assendelft et al., Cell 56: 969–977 (1989).
Grosveld et al., Cell 51: 975–985 (1987).
Gordon et al., Bio Technology 5: 1183–1187 (1987).
Hofmann et al., Science 239: 1277–1281 (1988).

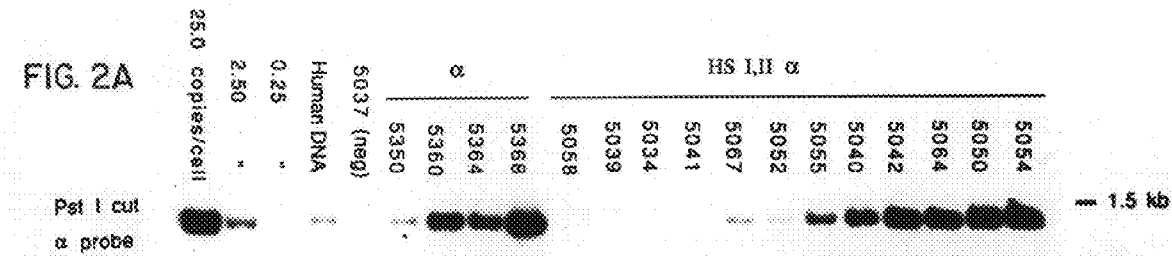
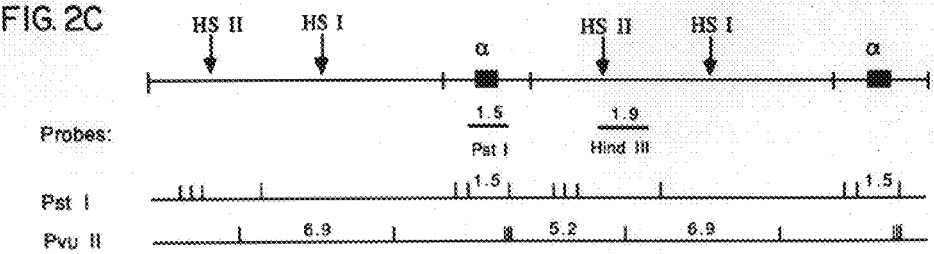

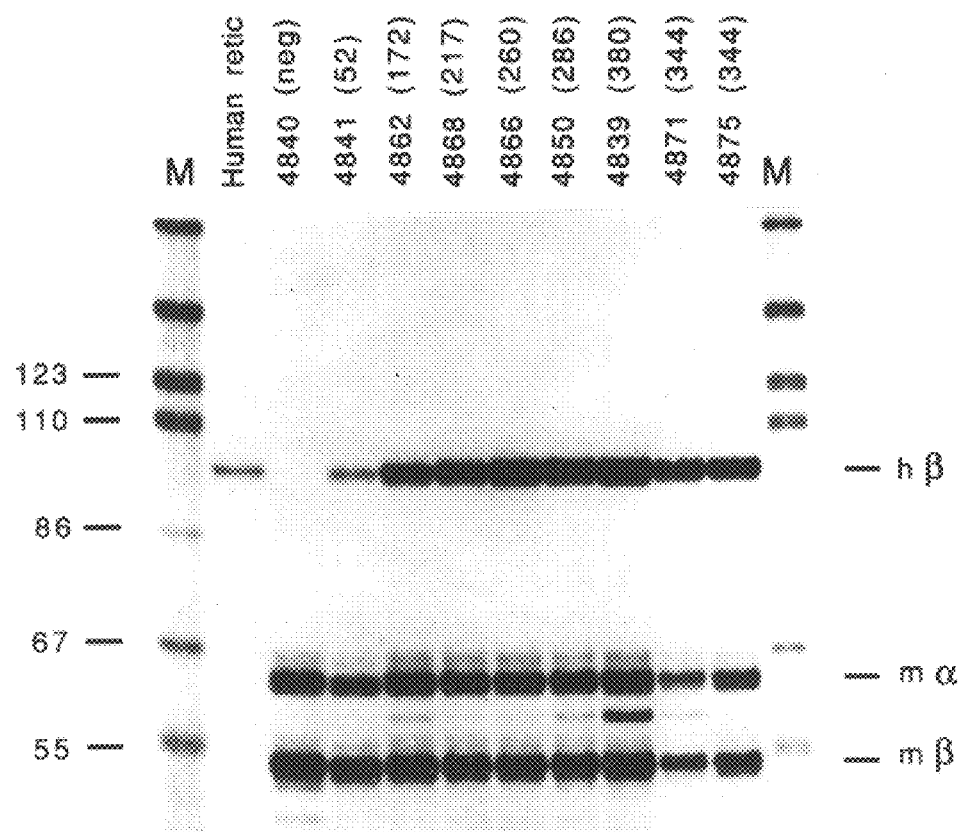
FIG. 10
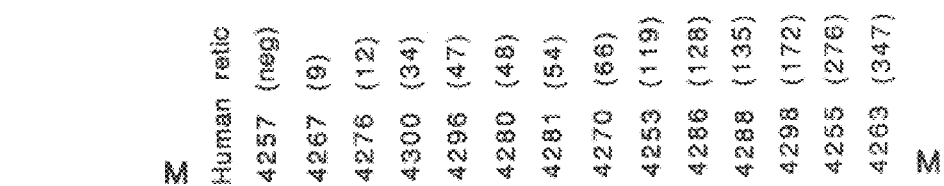
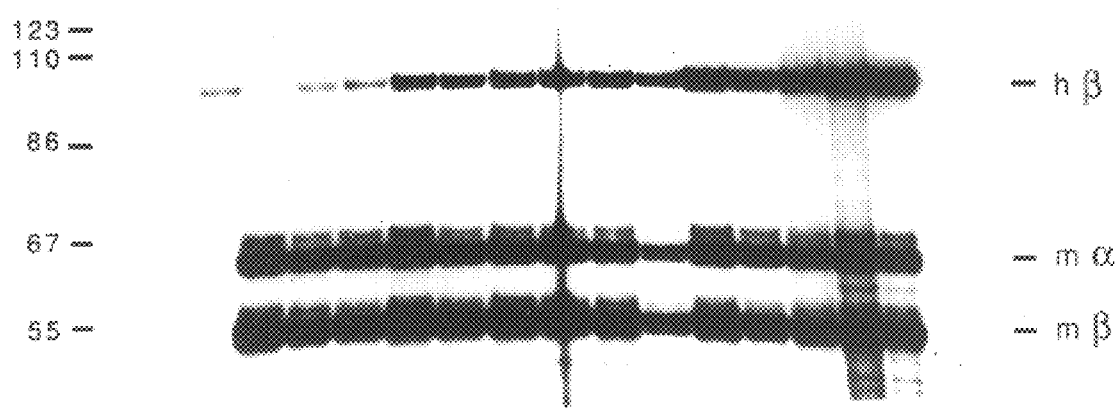
FIG. 11

NUCLEIC ACID VECTORS COMPRISING DNASE I HYPERSENSITIVE SITES

This application is a divisional of copending application Ser. No. 08/275,313, now U.S. Pat. No. 5,602,306, filed Jul. 13, 1994, which is a continuation of application Ser. No. 07/923,007, filed Jul. 30, 1992, now abandoned, which is a continuation of application Ser. No. 07/472,531, filed Jan. 30, 1990, now abandoned, which is a continuation-in-part of application Ser. No. 07/412,977 filed Sep. 26, 1989, now abandoned.

TABLE OF CONTENTS

1. Introduction
2. Background Of The Invention
   2.1. Globin Genes And Hemoglobin
      2.1.1. α and β Globin Genes
      2.1.2. DNase I Hypersensitivity Sites
   2.2. Transgenic Animals
   2.3. Expression Of Globin Genes In Transgenic Animals
3. Summary Of The Invention
   3.1. Definitions
4. Description Of The Figures
5. Detailed Description Of The Invention
   5.1. Globin Genes And Recombinant Vectors
      5.1.1. Genes Of Interest Which May Be Used According To The Invention
      5.1.2. Globin Genes
      5.1.3. DNase I Hypersensitivity Sites
      5.1.4. Cloning Of The Recombinant DNA Molecules Of The Invention
   5.2. Generation Of Transgenic Animals
   5.3. Transformation Of Cell Lines
   5.4. Expression Of Proteins In Erythroid Cells And Harvesting Of Protein
   5.5. Utility Of The Invention
      5.5.1. Transgenic Animal Models For Human Hemoglobinopathies
      5.5.2. Vectors Of The Invention In Gene Therapy
6. Example: High-Level Erythroid Expression Of Human a-Globin Genes In Transgenic Mice
   6.1. Materials And Methods
      6.1.1. a-Globin And HS I, II α-Globin Constructs
      6.1.2. Sample Preparation And Microinjection
      6.1.3. DNA Analysis
      6.1.4. RNA Analysis
   6.2. Results
      6.2.1. Production Of Human α-Globin And HS I, II α-Globin Transgenic Mice
      6.2.2. Expression Of Human α-Globin mRNA In HS I, II α-Globin Transgenic Mice
      6.2.3. Tissue Specificity Of HS I, II α-Globin Transgene Expression
   6.3. Discussion
7. Example: A Single Erythroid-Specific DNase I Super-Hypersensitive Site Activates High Levels Of Human β-Globin Gene Expression In Transgenic Mice
   7.1. Materials And Methods
      7.1.1. Construction of HS β-Globin Clones
      7.1.2. Sample Preparation And Microinjection
      7.1.3. DNA Analysis
      7.1.4. RNA Analysis
   7.2. Results
      7.2.1. Production of HS β-Globin Transgenic Mice
      7.2.2. Expression of Human β-Globin mRNA in HS-β-Transgenic Mice
      7.2.3. Tissue Specificity of HS β-Globin Transgene Expression
   7.3. Discussion
      7.3.1. Summary of HS β-Globin Expression
      7.3.2. Role of Individual Hypersenstivity Sites
      7.3.3. HS Site Effect On Other Genes
      7.3.4. Human β-Globin Domain
      7.3.5. Model for Developmental Regulation
8. Example: Synthesis Of Functional Human Hemoglobin In Transgenic Mice
   8.1. Materials And Methods
      8.1.1. α and β-Globin Gene Constructs
      8.1.2. Generation Of Transgenic Animals
   8.2. Results
      8.2.1. Tissue Specific Expression Of α and β-Globin Transgenes
      8.2.2. Identification Of Human Hemoglobin In Transgenic Mice
      8.2.3. Functional Properties Of Human Hemoglobin In Transgenic Mice
   8.3 Discussion
9. Example: Expression of Human Sickle Hemoglobin In Transgenic Mice
   9.1. Materials and Methods
      9.1.1. DNA Constructs
      9.1.2. Sample Preparation And Microinjection
   9.2. Results and Discussion
10. Example: Expression of LAC Z in Erythroid Cells of Transgenic Mice
11. Deposit of Cosmid DNAs

1. INTRODUCTION

The present invention relates to the synthesis of functional human hemoglobin and other proteins in erythroid tissues of transgenic non-human animals or erythroid cell lines. In addition, the present invention provides for novel expression vectors which may be used to produce α-globin as well as other proteins of interest in quantity in the red blood cells of transgenic animals or erythroid cell lines; these proteins may subsequently be purified and utilized for a multitude of purposes. The human hemoglobin produced in transgenic animals according to the invention can be used as an effective, nonimmunogenic red blood cell substitute for transfusion in humans which is free of hepatitis virus and human retrovirus contamination.

2. BACKGROUND OF THE INVENTION

2.1. Globin Genes and Hemoglobin

Native hemoglobin exists as a tetrameric protein consisting of two α chains and two β chains. Each α and β chain binds a heme residue in noncovalent linkage. The α and β chains are also held together by noncovalent bonds resulting from hydrogen bonding and Van der Waals forces. Hemoglobin constitutes about 90% of the total protein in red blood cells; 100 ml of whole blood is capable of absorbing approximately 21 ml of gaseous oxygen.

2.1.1. α and β Globin Genes

Different molecular species of hemoglobin are produced during the embryonic, fetal, and adult life of an animal. The genes encoding the globin molecules expressed during the various developmental stages are arranged in clusters. In humans and most other mammals the α and β-like gene clusters are arranged in order of their expression during development, with the embryonic genes followed by the fetal and adult globin genes (Watson et al., 1987, in "Molecular Biology of the Gene", Fourth Edition, The Benjamin/Cummings Publishing Co., Inc., Menlo Park, Calif., p. 650). This developmental order is not obligatory, however; for example, in the chicken, the adult β-globin genes are flanked by embryonic genes.

In humans, the α globin gene cluster is located on chromosome 16 and the β globin gene cluster is located on chromosome 11. The human β globin gene cluster comprises one embryonic (ε), two fetal ($^G\gamma$ and $^A\gamma$) and two adult δ and β) globin genes, which reside within approximately 50 kb of chromosomal DNA in the order 5'-ε-$^G\gamma$-$^A\gamma$-δ-β-3' (Fritsch et al., 1980, Cell 19:959–972).

Expression of the human β-like globin genes is precisely regulated in three important ways; they are expressed only in erythroid tissue, only during defined stages of development, and are produced at very high levels so as to rapidly establish the developmentally appropriate hemoglobin as the dominant protein in the red blood cell. The process by which the red blood cell ceases to transcribe one particular globin gene and begins to express another is referred to as "hemoglobin switching". A great deal of study has been directed toward the regulatory mechanisms responsible for the switching process.

Research has indicated that DNA sequences involved in the regulation of human β-globin gene expression are located both 5' and 3' to the translation initiation site (Wright et al., 1984, Cell 38:251–263). Analysis of constructs with β-globin gene fragments inserted upstream of a reporter gene have demonstrated that sequences located immediately upstream, within, and downstream of the gene contribute to the correct temporal and tissue specific expression (Behringer et al., 1987, Proc. Natl. Acad. Sci. U.S.A. 84:7056–7060; Kollias et al., 1987, Nucl. Acids Res. 15:5739–5747). Using murine erythroleukemia (MEL) and K562 cells, at least four separate regulatory elements required for appropriate expression of the human β-globin gene have been identified: (i) a globin specific promoter element; (ii) a putative negative regulatory element, and (iii and iv) two downstream regulatory sequences with enhancer-like activity, one of which is located in the second intron of the β-globin gene and the other located approximately 800 basepairs (bp) downstream of the gene (Behringer et al., 1987, Proc. Natl. Acad. Sci. U.S.A. 84:7056–7060). Hesse et al. (1986, Proc. Natl. Acad. Sci. U.S.A. 83:4312–4316) identified a similar enhancer sequence downstream of the chicken β-globin gene in cultured chicken erythroid cells (see also Choi and Engel, 1986, Nature 323:731–734).

2.1.2. DNase I Hypersensitivity Sites

Active chromatin domains have been associated with overall sensitivity to DNase I digestion relative to unexpressed genes or DNA outside the active chromatin domain. Hypersensitivity sites are superimposed on the increased sensitivity of active chromatin; these DNase I hypersensitivity (HS) sites comprise approximately 100 to 200 bp of DNA which are highly susceptible to cleavage by the nuclease action of DNase I. DNase I hypersensitive sites are mapped by (i) treating nucleic acid with DNase I; (ii) isolating DNA from the nuclei; (iii) digesting the isolated DNA with a restriction enzyme; (iv) fractionating the restriction enzyme-cut DNA (i.e. by gel electrophoresis); (v) blotting the fractionated DNA on nitrocellulose; and (vi) hybridizing the nitrocellulose with a labeled probe corresponding to a subfragment of nucleic acid sequence located near the gene of interest. In addition to the full length fragment generated by the restriction enzyme, a multitude of shorter bands generated by DNase I will appear if the probe represents an area of the DNA contained in a DNase I hypersensitive site (Watson et al., 1987, in "Molecular Biology of the Gene," Fourth Edition, The Benjamin/Cummings Publishing Co., Menlo Park, Calif., pp. 692–693).

Figure 5:
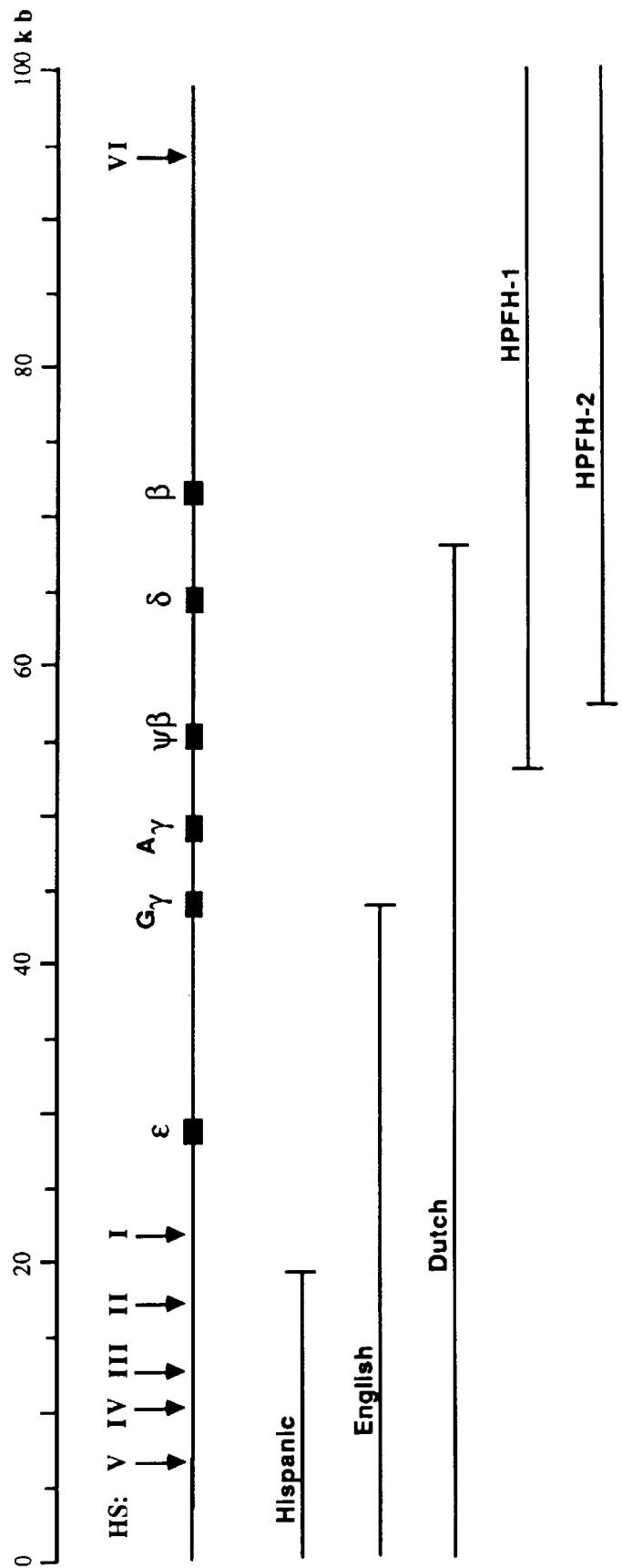

Several years ago, Tuan et al. (1985, Proc. Natl. Acad. Sci. U.S.A. 82:6384–6388) and Forrester et al. (1986, Proc. Natl. Acad. Sci. U.S.A. 83:1359–1363) mapped sites that were super-hypersensitive to DNase I digestion 6–22 kilobases (kb) upstream of the ε-globin gene and 19 kb downstream of the β-globin gene. The sites were found specifically in erythroid tissue at all stages of development. FIG. 5 depicts the location of these sites in the human β-globin locus. Tuan et al. (1985, Proc. Natl. Acad. Sci. U.S.A. 82:6384–6388) observed that the major DNase I hypersensitive sites, HS I, HS II, and HS IV, situated upstream of the β-globin gene, appeared to be strongly associated with β-like globin gene expression since they were found to be present in K562 cells, human erythroleukemia cells, and adult human nucleated bone marrow cells (which express β-like globin genes) but to be absent in HL60 cells, which do not express the β-like globin genes. These experiments suggest that the super-hypersensitive sites define locus activation regions which open a large chromosomal domain for expression specifically in erythroid cells and thereby dramatically enhance globin gene expression. Furthermore, the structure of mutant loci from patients with several hemoglobinopathies suggests that the upstream hypersensitivity sites are required for efficient β-globin gene expression in humans. English and Dutch $_\gamma$δβ-thalassemia appears to result from deletions that remove all of the upstream hypersensitivity sites (FIG. 5); although the β-globin gene is intact in these patients, no β-globin mRNA is produced from the mutant alleles.

2.2. Transgenic Animals

The term "transgenic animals" refers to non-human animals which have incorporated a foreign gene into their genome; because this gene is present in germline tissues, it is passed from parent to offspring. Exogenous genes are introduced into single-celled embryos (Brinster et al., 1985, Proc. Natl. Acad. Sci. U.S.A. 82:4438–4442). Transgenic mice have been shown to express globin (Wagner et al., 1981, Proc. Natl. Acad. Sci. U.S.A. 78:6376–6380), transferrin (McKnight et al., 1983, Cell 34:335–341), immunoglobulin (Brinster et al., 1983, Nature 306:332–336; Ritchie et al., 1984, Nature 312:517–520; Goodhardt et al., 1987, Proc. Natl. Acad. Sci. U.S.A. 84:4229–4233; Stall et al., 1988, Proc. Natl. Acad. Sci. U.S.A. 85:3546–3550), human major histocompatibility complex class I heavy and light chain (Chamberlain et al., 1988, Proc. Natl. Acad. Sci. U.S.A. 85:7690–7694, functional human interleukin-2 receptors (Nishi et al., 1988, Nature 331:267–269, rat myosin light-chain 2 (Shani, 1985, Nature 314:283–286), viral oncogene (Small et al., 1985, Mol. Cell. Biol. 5:642–648), and hepatitis B virus (Chisari et al., 1985, Science 230:1157–1163) genes, to name but a few. Rearrangement of immunoglobulin genes has been observed in transgenic mice (Goodhardt et al., 1987, Proc. Natl. Acad. Sci. U.S.A. 84:4229–4233; Bucchini et al., 1987, Nature 326:409–411). Krimpenfort et al. (1987, EMBO J. 6:1673–1676) generated transgenic mice that showed cell surface expression of HLA-B27 antigen biochemically indistinguishable from HLA-B27 in human cells by crossing one strain of transgenic mice carrying the HLA-B27 heavy chain gene with mice carrying the transgenic $\beta_2$ microglobulin gene.

2.3. Expression OF Globin Genes IN Transgenic Animals

Correctly regulated expression of human $\beta$-globin genes in transgenic mice has been observed with expression of the human gene occurring only in murine erythroid tissue (Townes et al., 1985, EMBO J. 4:1715–1723; Townes et al., 1985, Mol. Cell Biol. 5: 1977–1983). Despite inclusion of the promoter and several enhancer sequences, however, human $\beta$-globin transgenes were not found to be expressed at the same levels as mouse $\beta$-globin; in many cases, transgenic animals expressing the highest levels of human $\beta$-globin were those which carried the greatest number of transgenes per cell. Grosveld et al. (1987, Cell 51:975–985) observed that high levels of human $\beta$-globin gene expression could be obtained in transgenic animals carrying a single copy of the transgene if sequences at the extreme ends of the human globin locus were included in the injected construction. When these sequences, which include the erythroid-specific DNase I super-hypersensitive sites, were fused upstream of the human $\beta$-globin gene and injected into fertilized mouse eggs, large amounts of human $\beta$-globin mRNA were synthesized and virtually all transgenic mice which developed expressed high levels of human $\beta$-globin (Grosveld et al., 1987, Cell 51:975–985; Ryan et al., 1989, Genes and Development 3:314–323; Behringer et al., 1989, Science 245:971–973; Talbot et al., 1989, Nature 338:352). Correctly regulated mouse and human $\beta$-globin gene expression in cultured cells (Spandidos, et al., 1982, EMBO J. 1:15–20; Chao, et al., 1983, Cell 32:483–493; Wright et al., 1983, Nature 305:333–336) and transgenic mice (Chada, et al., 1985, Nature 314:377–380; Magram, et al., 1985, Nature 315:338–340; Townes et al., 1985, EMBO J. 4:1715–1723; Townes et al., 1985, Mol. Cell. Biol. 5:1977–1983; Costantini et al, 1985, Cold Spring Harbor Symp. Quant. Biol. 50:361–370; Kollias, et al., 1986, Cell. 46:89–94) is well documented. However, correctly regulated human $\alpha$-globin gene expression has been difficult to achieve. Although the $\alpha$-globin genes in humans are expressed exclusively in erythroid tissue, high levels of transcription from transfected $\alpha$-globin genes are obtained in nonerythroid culture cells (Triesman et al., 1983, Proc. Natl. Acad. Sci. U.S.A. 80:7428–7432; Treisman et al., 1984, Cell 38:251–263). In these same nonerythroid cells, expression of transfected $\beta$-globin genes requires cis- or trans-activation by nonglobin sequences (Charney et al., 1984, Cell 38:251–263; Banerjii et al., 1981, Cell 27:299–308; Green et al., 1983, Cell 35:137–148). Transfected human $\beta$-globin genes are expressed at low levels in uninduced murine erythroleukemia (MEL) cells but are transcribed at high levels when these cells are induced to differentiate (Spandidos, et al., EMBO J. 1:15–20; Chao et al., Cell 32:483–493; Wright et al., 1983, Nature (London) 305:333–336). Transfected $\alpha$-globin genes, on the other hand, are expressed at the same high level in uninduced and induced MEL cells (Charney et al., 1984, Cell 38:251–263). This phenomenon is observed even if the $\alpha$ and $\beta$-globin genes are introduced into cells on the same plasmid (Charney et al., 1984, Cell 38:251–263).

Based on the results from cultured cells, $\alpha$-globin genes might be expected to express at high levels in transgenic mice, possibly in nonerythroid as well as in erythroid tissues. However, this has not been the case. Transgenic animals have been created that carry the human $\alpha$1-globin gene on a 3.8-kilobase (kb) Bgl II-EcoRI fragment, the $\alpha$2- and $\alpha$1-globin genes on a 14-kb Bam-HI fragment, the entire human $\alpha$-globin locus on a 42-kb cosmid fragment, and the human $\alpha$- and $\beta$-globin genes in various orientations on the same fragment. Although 61 animals that contain intact copies of these transgenes have been obtained, no a-globin mRNA has been detected in any tissue.

Researchers have endeavored to develop transgenic animals that may be used as models for human hemoglobinopathies. Mouse models for thalassemia have been developed ($\alpha$-thalassemia: Martinell et al., 1981, Proc. Natl. Acad. Sci. U.S.A. 78:5056–5060; $\beta$-thalassemia: Skaw et al., 1983, Cell 34:1043–1052) from spontaneous mutations of the murine $\alpha$ and $\beta$-globin genes; however, the development of animal models carrying the exact mutations found in human hemoglobinopathies, such as, for example, thalassemia, is problematic. Rubin et al. (1988, Am. J. Hum. Genet. 42:585–591 and 1988, J. Clin. Invest. 82:1129–1133) developed a strain of transgenic mice carrying the human $\beta^S$-globin (sickle hemoglobin) gene. Red blood cells from these mice have not been found to exhibit the sickle cell conformation; however, they have been crossed with a strain of thalassemic mice in order to study the physiology of thalassemia.

3. SUMMARY OF THE INVENTION

The present invention relates to the synthesis of functional human hemoglobin and other proteins in erythroid tissues of transgenic non-human animals and erythroid cell lines. It is based on the discovery that two of the five hypersensitivity sites of the $\beta$-globin locus are sufficient to result in high level expression of human $\alpha$- or $\beta$-globin transgenes.

The present invention also provides for novel recombinant nucleic acid vectors which may be used to produce $\alpha$-globin as well as other proteins of interest in quantity in the red blood cells of transgenic animals or cell cultures of erythroid lineage. The present invention also provides for the transgenic animals which contain these recombinant nucleic acid vectors. The vectors of the invention comprise at least one of the major DNase I hypersensitivity sites associated with the $\beta$-globin locus together with a gene of interest; in preferred embodiments of the present invention, a vector comprises two of the major DNase I hypersensitivity sites associated with the $\alpha$-globin locus. According to various embodiments of the invention, the vectors may be used to create transgenic animals or to transfect cells in culture. In a specific embodiment of the invention, a vector which comprises two DNase I hypersensitivity sites together with the human $\alpha$-globin gene is used to create transgenic animals which produce human $\alpha$-globin protein in erythroid tissues, including red blood cells. In a preferred specific embodiment of the invention, transgenic animals are created which comprise human $\alpha$-globin and $\beta$-globin genes, each under the transcriptional influence of two $\beta$-globin locus DNase I hypersensitivity sites; these transgenic animals express human hemoglobin in their erythroid tissues, and can be used to produce human hemoglobin in quantity. In another preferred specific embodiment of the invention, transgenic animals are created which comprise the lac Z gene under the influence of $\beta$-globin DNase I hypersensitivity sites, and which express the lacZ enzyme in their red blood cells.

Proteins of interest, including, but not limited to, human hemoglobin, encoded by the transgenes of the invention may be harvested in quantity from the red blood cells of transgenic animals. By including an erythroid-specific transcriptional signal in transgenes comprising a gene encoding the protein of interest, the present invention advantageously exploits the genetic programming of the red blood cell, which devotes almost its entire synthetic capabilities to the production of hemoglobin.

Human hemoglobin produced according to the methods of the present invention may be used as a red blood cell substitute in humans. Because the hemoglobin of the invention is identical to native human hemoglobin, it is nonimmunogenic; because it is produced in non-human animals, it is free of such human pathogens as hepatitis virus and human retroviruses, including human immunodeficiency virus (HIV) and human T-cell leukemia virus (HTLV). Production of human hemoglobin in transgenic animals offers the additional advantage of providing a red blood cell substitute which can be used to transfuse patients having any blood type whatsoever, thereby obviating the persistent problems created by limited availability of transfusable blood for rare or relatively unusual blood types.

3.1. Definitions transgenic animal: a nonhuman animal which has incorporated a foreign gene into its genome.

transgene=transgenic sequence: a foreign gene or recombinant nucleic acid construct which has been incorporated into a transgenic animal.

4. DESCRIPTION OF THE FIGURES

FIG. 1. α-globin and HS I, II α-globin construction. A 12.9-kb Mlu I-Cla fragment containing HS sites I and II from the human β-globin locus was inserted into a modified pUC19 plasmid upstream of a 3.8-kb Cla I-Sal II fragment containing the human al-globin gene. The α1-globin gene was originally obtained as a Bgl I-EcoRI fragment. The 16.7-kb Mlu I-Sal I fragment containing HS I, II α-globin and a 3.8-kb fragment containing α-globin alone were separated from plasmid sequences and injected into fertilized mouse eggs as described by Brinster et al. (1985, Proc. Natl. Acad. Sci. U.S.A. 82:4438–4442).

FIG. 2A, 2B, 2C. Southern blot analysis of α-globin and HS I, II α-globin transgenic mice. Ten micrograms of fetal liver DNA was digested with Pst I (A) or Pvu II(B) separated on 1.0% agarose gels. After blotting to nitrocellulose, the samples were hybridized with the human α-globin and HS II-specific probes illustrated in C (solid bars). (A) Lanes 1–3 are herring sperm DNA spiked with the equivalent of 25, 2.5 and. 0.25 copies per cell of the α-globin construct, respectively. Lane 4 is 10 μg of human DNA, and lane 5 is fetal liver DNA from a nontransgenic mouse control (5037). Filters were exposed to film for 12 hours at −70° C. with an intensifying screen. (B) Lanes 1–4 were exposed for 96 hours to reveal the absence of the 5.2-kb band in sample 5058. (C) A map of head-to-tail tandem copies of the HS I, II α-globin transgene. Pst I and Pvu II sites are listed below the construct. Solid bars represent the 1.5-kb globin and 1.9-kb HS II-specific probes used in the Southern blot hybridizations illustrated above.

Figure 3:
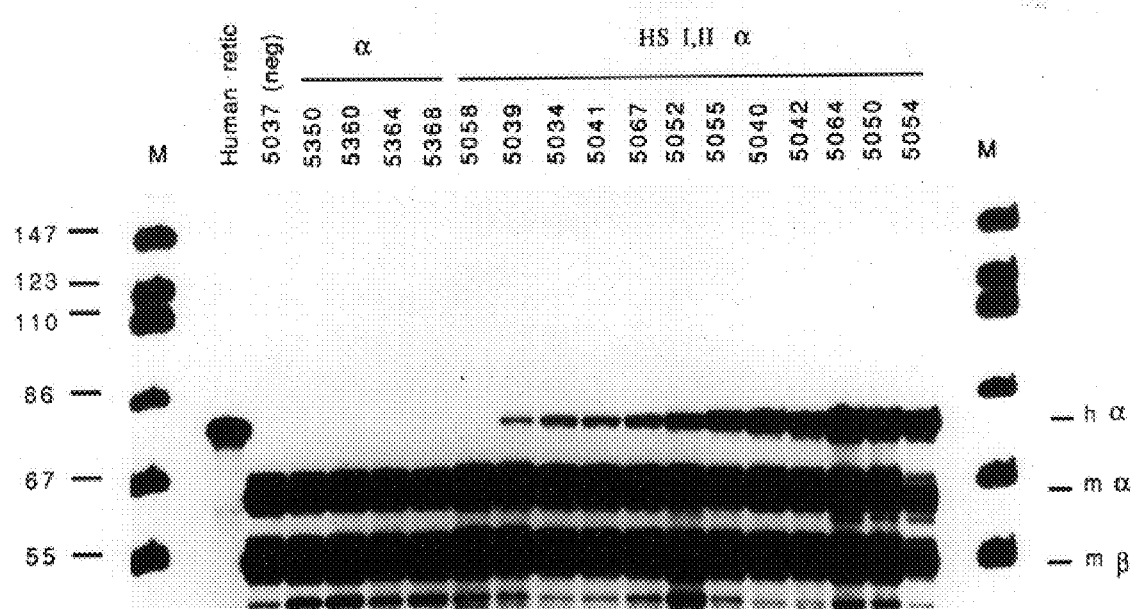

FIG. 3. Primer extension analysis of fetal liver RNA from α-globin and HS I, II α-globin transgenic mice. Human (h) α-globin, mouse (m) α-globin, and mouse β-globin-specific oligonucleotides were end-labeled with [α-$^{32}$P]ATP(3000 Ci/mmol: 1 Ci=37 GBq) and hybridized together with 5 μg of fetal liver RNA or 0.5 μg of reticulocyte RNA and then extended with reverse transcriptase to map the 5' ends of human α-globin, mouse α-globin, and mouse β-globin mRNA. The products were electrophoresed on a 8.0% urea/polyacrylamide gel. The gel was autoradiographed for 8 hours at −70° C. with an intensifying screen. Markers (M) are end-labeled Hpa II fragments of the plasmid pSP64.

Figure 4:
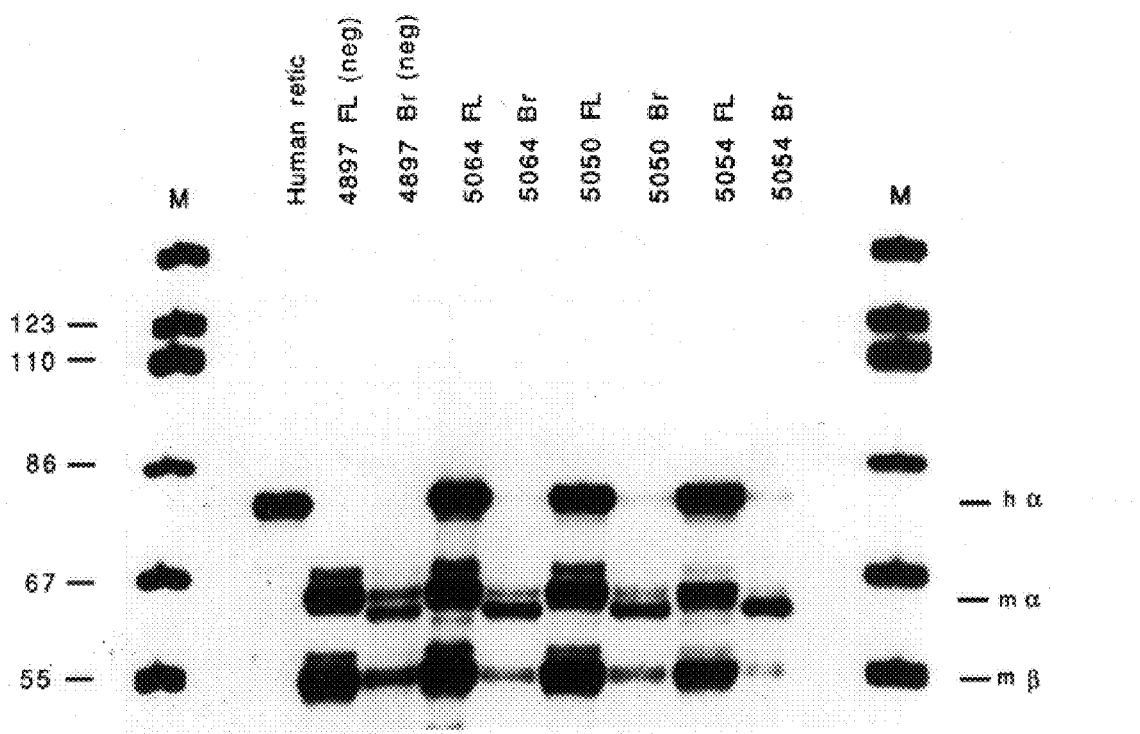

FIG. 4. Tissue specificity of HS I,II α-globin expression. Primer extension analysis of fetal liver and brain RNA from the three highest HS I, II α-globin expressors (5064, 5050, and 5054) was performed as described in FIG. 3 to assess the tissue specificity of HS I, II α-globin transgene expression. Mouse 4897 is a non-transgenic negative control. Br. brain; FL. fetal liver; retic. recticulocyte; m. mouse; h. human.

FIG. 5. Human β-globin locus. A 100 kb region of human chromosome 16 containing the β-like globin genes is illustrated. Erythroid-specific HS sites located 6–22 kb upstream of ε and 19 kb downstream of β are marked by arrows (Tuan et al., 1985, Proc. Natl. Acad. Sci. U.S.A. 82:6384–6388; Forrester et al., 1987, Nucleic Acids Res. 15:10159–10177). The lines beneath the locus represent deletions involved in Hispanic, English, and Dutch γδβ-thalassemias and two deletion forms of HPFH (Bunn and Forget, 1986; Stamatoyannopoulos et al., 1987, Nucleic Acids Res. 15:10159–10177). The Hispanic patent described by C. Driscoll et al. has a β$^S$ allele on the affected chromosome but does not make any sickle hemoglobin.

Figure 6:
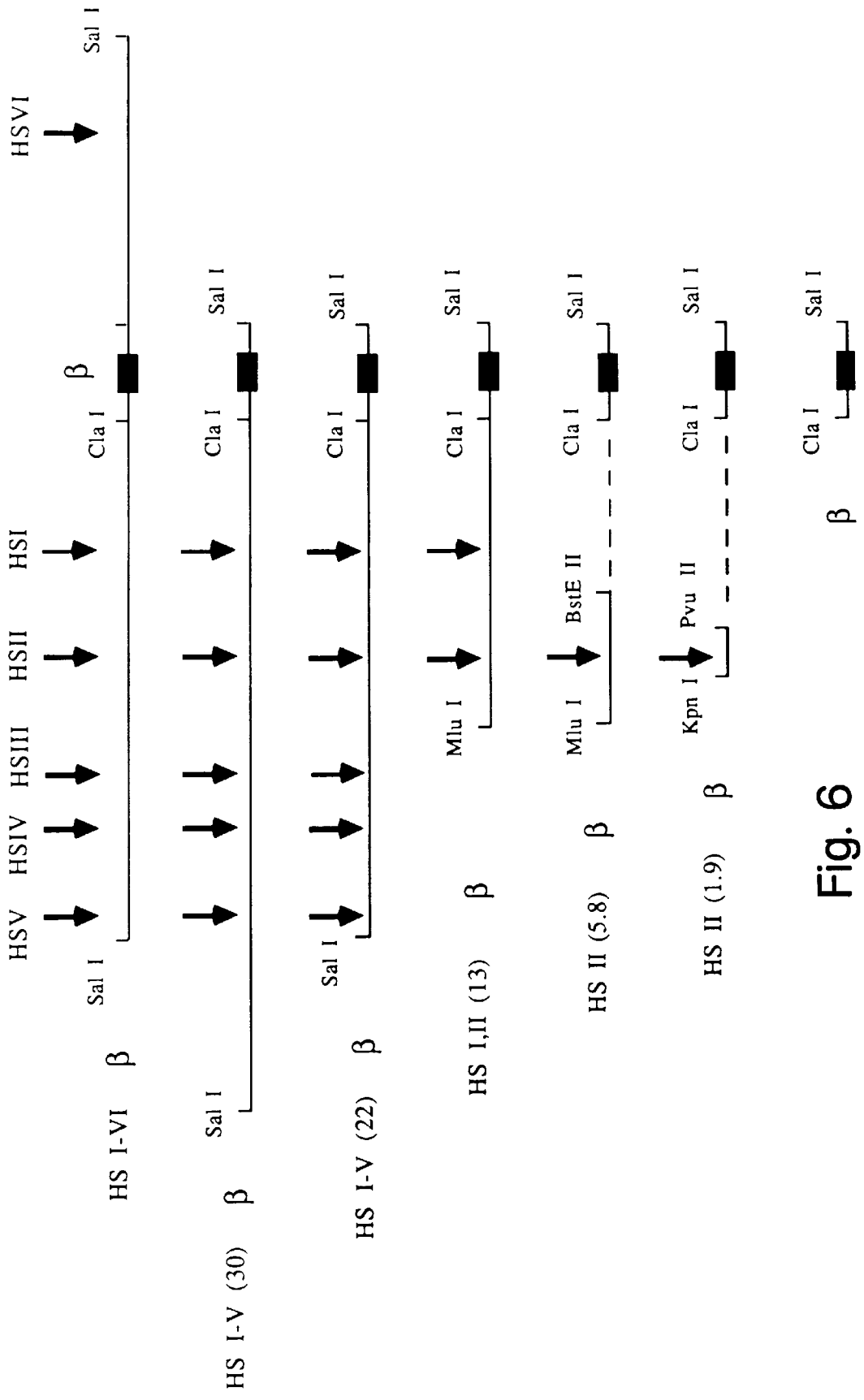

FIG. 6. HS β and β constructs injected into fertilized mouse eggs. HS I-VI β, HS I-V (30) β, and HS I-V (22) β were constructed from λ clone fragments containing the HS sequences (Li et al., 1985, J. Biol. Chem. 260:14901–14910). The numbers in parentheses represent the sizes of the upstream fragments in kilobase pairs. These fragments and a fragment containing the human β-globin gene were inserted into the plasmid vector pCV001. HSI, II (13) β and HS I (7.0)β were derived from the HS I-V (22)β cosmid clone. HS II (5.8)β and HS II (1.9) β were cloned as plasmids. The β-globin gene in all of these constructs is on a 4.1-kb Hpa-XbaI fragment containing 815 bp of 5'-flanking sequence and 1700 bp of 3'-flanking sequence. The HpaI site was changed to ClaI, and the XbaI site was changed to SalI in all constructs except HS I-VI β, where the XbaI site was changed to XhoI. In all cases, the fragments were cut out of cosmid or plasmid clones, purified from vector sequences on low gelling temperature agarose gels, and microinjected into fertilized mouse eggs as described by Brinster et al. (1985, Mol. Cell. Biol. 5:1977–1983).

Figure 7A:
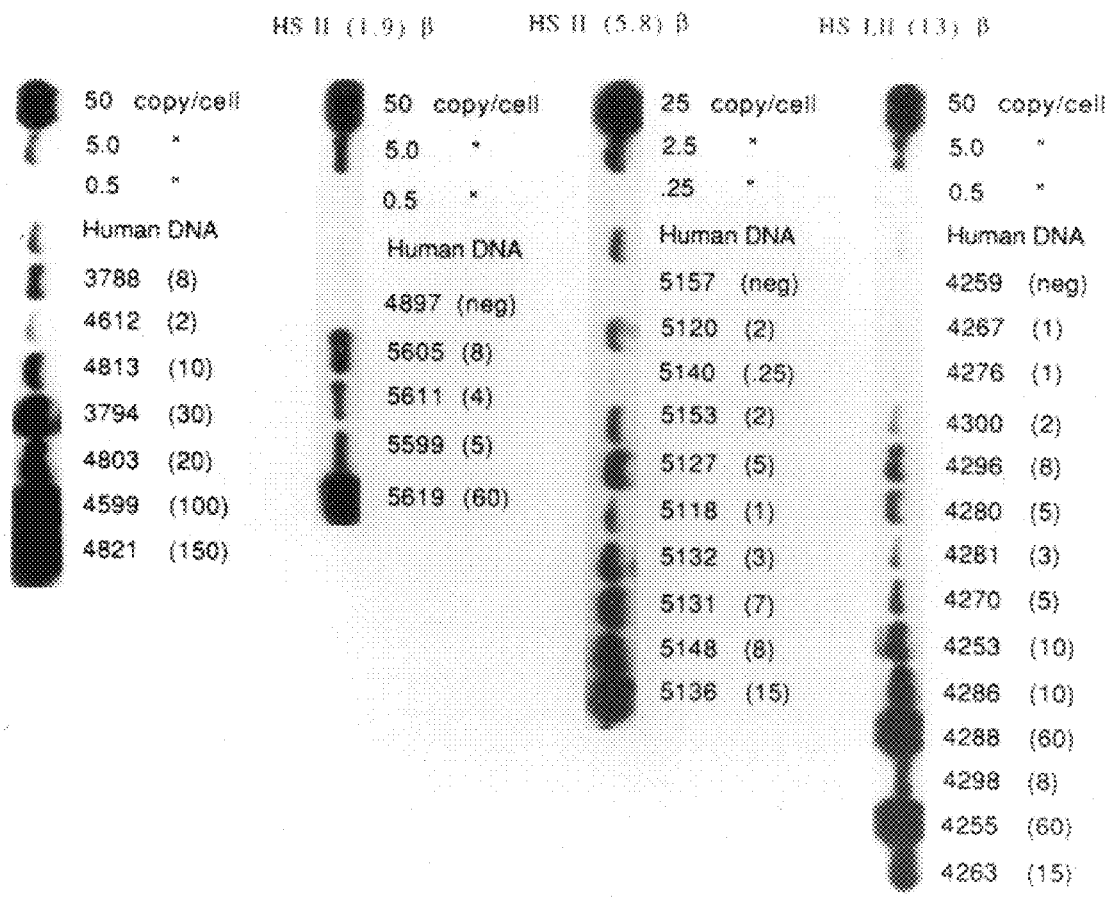
Figure 7B:
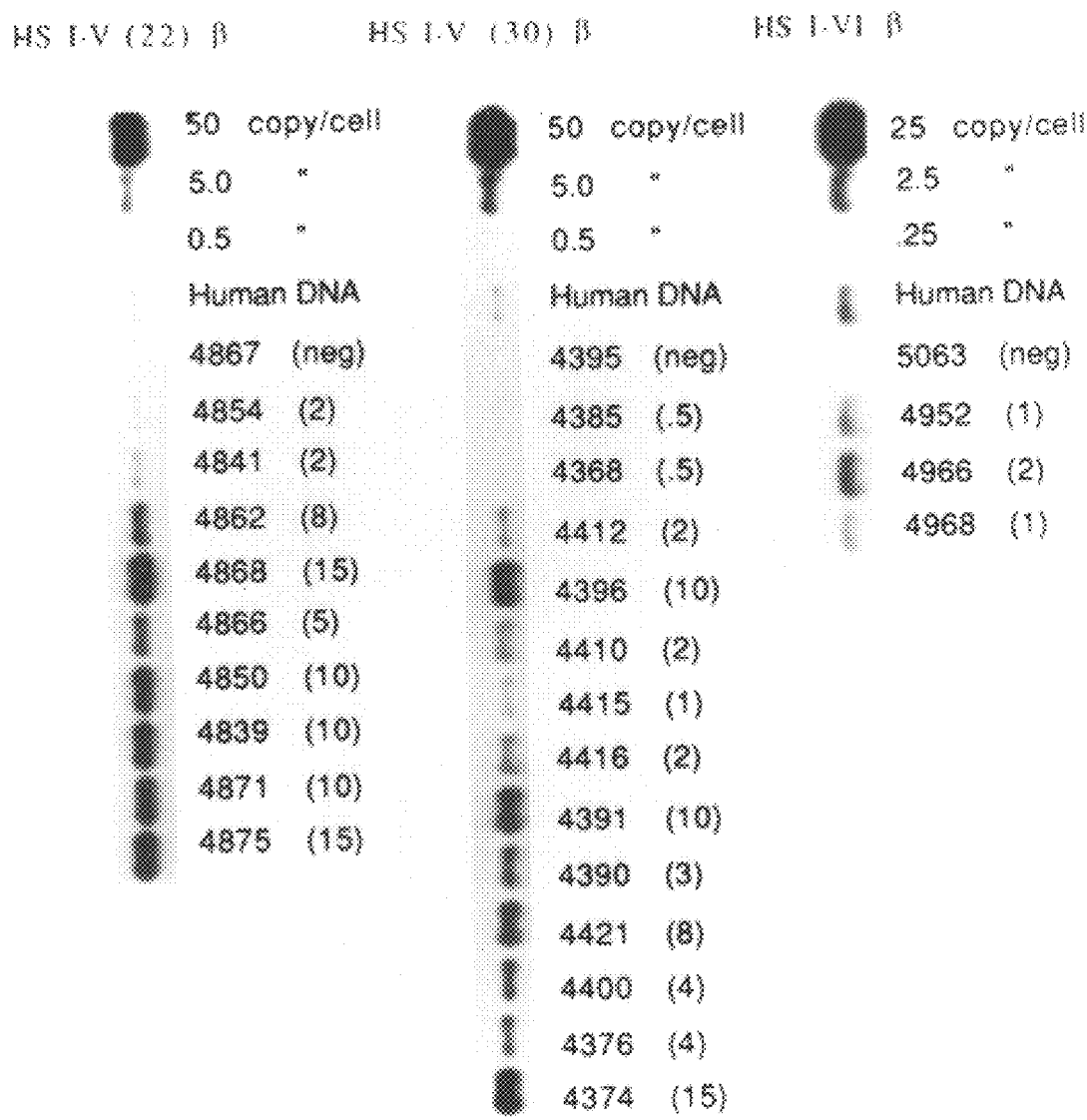

FIG. 7. Southern blot analysis of HS β and β transgenic mice. Ten micrograms of fetal liver DNA Or control DNA was digested with BamHI and PstI and separated on 1.0% agarose gels. After blotting onto nitrocellulose, the samples were hybridized with a human β-globin-specific probe derived from the second intron. (Lanes 1–3) Herring sperm DNA spiked with the equivalent of 50, 5.0, and 0.5 or 25, 2.5, and 0.25 copies per cell of the respective construct, (lane 4) human DNA; (lane 5) a nontransgenic mouse control. The single 1.7-kb band observed in all of the samples, except the negative controls, represents the fragment generated from digestion of the BamHI site in the second exon of the human β-globin gene and the PstI site located 559 bp downstream of the poly(A) site. The intensity of this band was compared to the standards in lanes 1–4 to determine transgene copy number. The number of copies per cell of the transgene is listed in parenthesis after each sample number.

Figure 8:
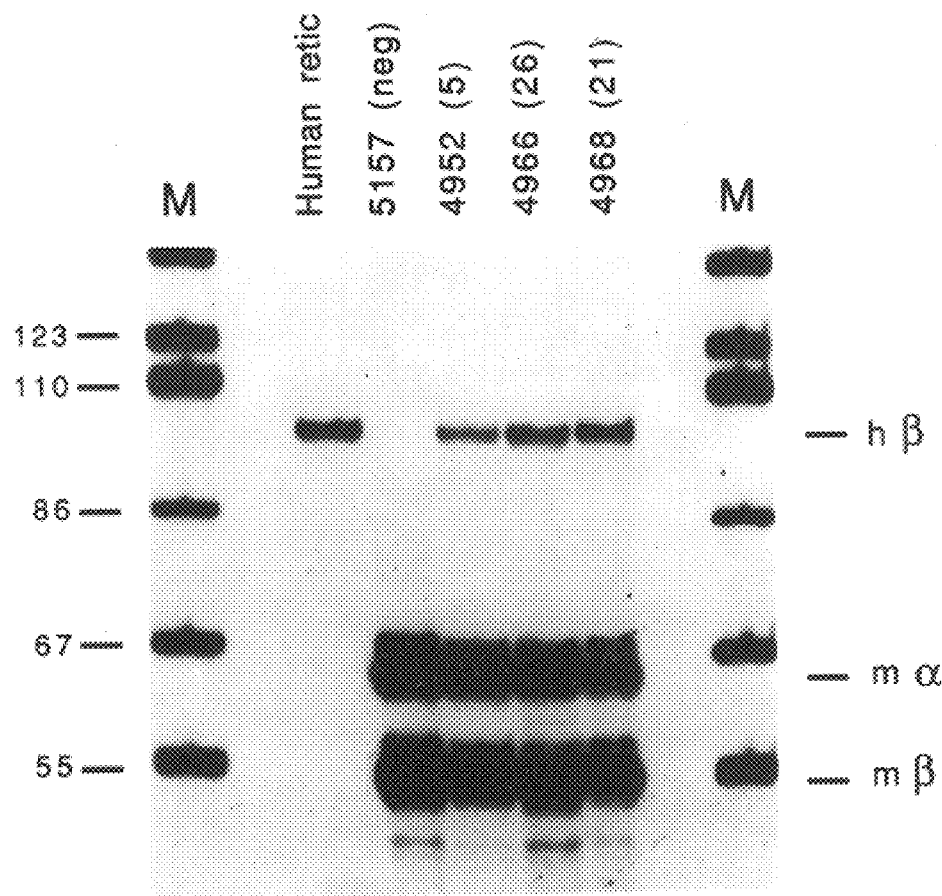

FIG. 8. Primer extension analysis of fetal liver. RNA from HS I-VI β transgeic mice. Human α-, mouse α-, and mouse β-globin-specific oligonucleotides were end labeled with (α-$^{32}$P)/ATP (3000 Ci/mM) and hybridized together with 5 μg of mouse fetal liver RNA or 0.5 μg or human reticulocyte RNA and then extended with reverse transcriptase to map the 5' ends of human β, mouse α, and mouse β-globin mRNAs. The products were electrophoresed on an 8.0% urea-polyacrylamide gel, and the gel was autoradiographed for 8 hr at −70° C. with an intensifying screen. The authentic human β-globin primer extension product is 98 bp. and the correct mouse α- and β globin products are 65 and 53 bp respectively. Markers are end-labeled HpaII fragments of the plasmid pSP64. Accurate quantitative values of human β-globin and mouse β-globin mRNAs were determined by solution hybridization with human β-globin and mouse β-globin-specific oligonucleotides. Levels of human β-globin mRNA expressed as a percentage of endogenous mouse β-globin mRNA are listed in parenthesis after each sample number.

Figure 9:
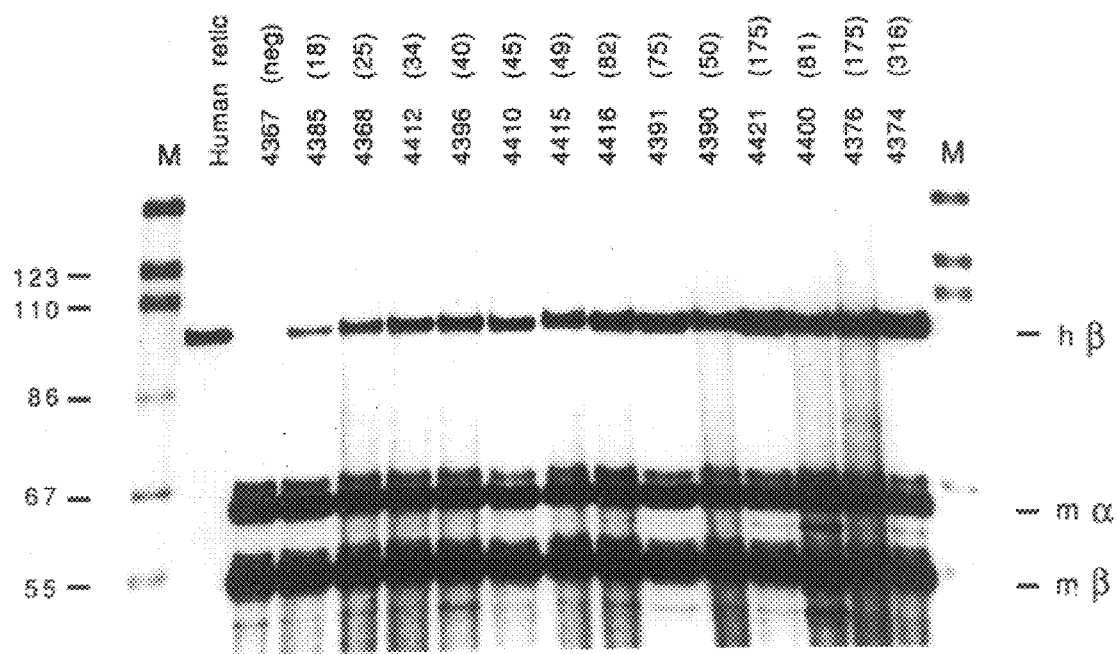

FIG. 9. Primer extension analysis of fetal liver RNA from HS I-V (30) β transgenic mice. As described in the legend to FIG. 8, 5 μg of fetal liver RNA was analyzed.

FIG. 10. Primer extension analysis of fetal liver RNA from HS-I-V (22) β transgenic mice. As described in the legend to FIG. 8, 5 μg of fetal liver RNA was analyzed.

FIG. 11. Primer extension analysis of fetal liver RNA from HS I, II (13) β transgenic mice. As described in the legend to FIG. 8, 5 μg of fetal liver RNA was analyzed.

Figure 12:
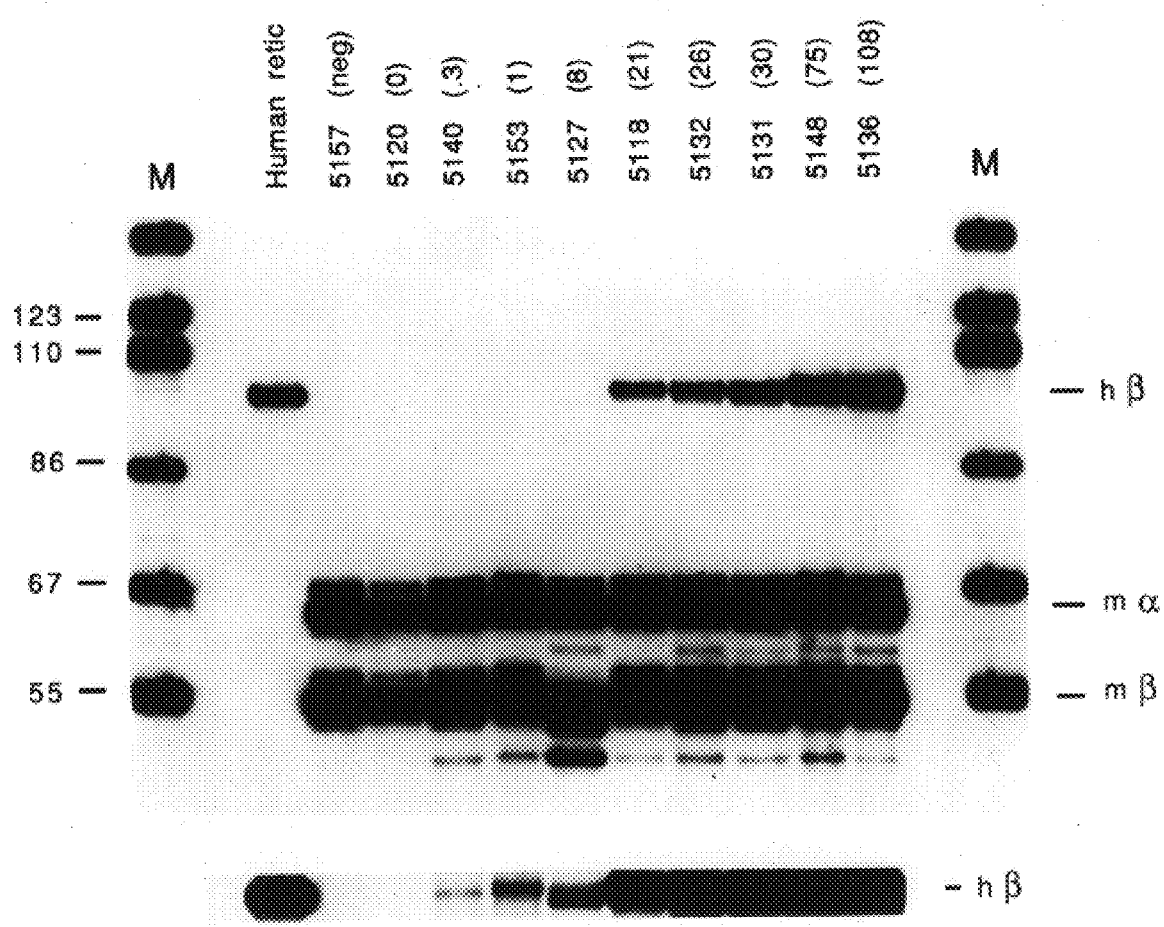

FIG. 12. Primer extension analysis of fetal liver RNA from HS, II (5.8) β transgenic mice. As described in the legend to FIG. 8, 5 μg of fetal liver RNA was analyzed. A 3-day exposure of the human β-globin, 98-bp primer extension product is shown in the insert. Samples 155140 and 5153 contained rearranged copies of the transgene and the RNA from sample 5127 was degraded slightly. Sample 5120 was the only one of 51 transgenic mice that contained an intact copy of the transgene but did not express any human β-globin mRNA.

Figure 13:
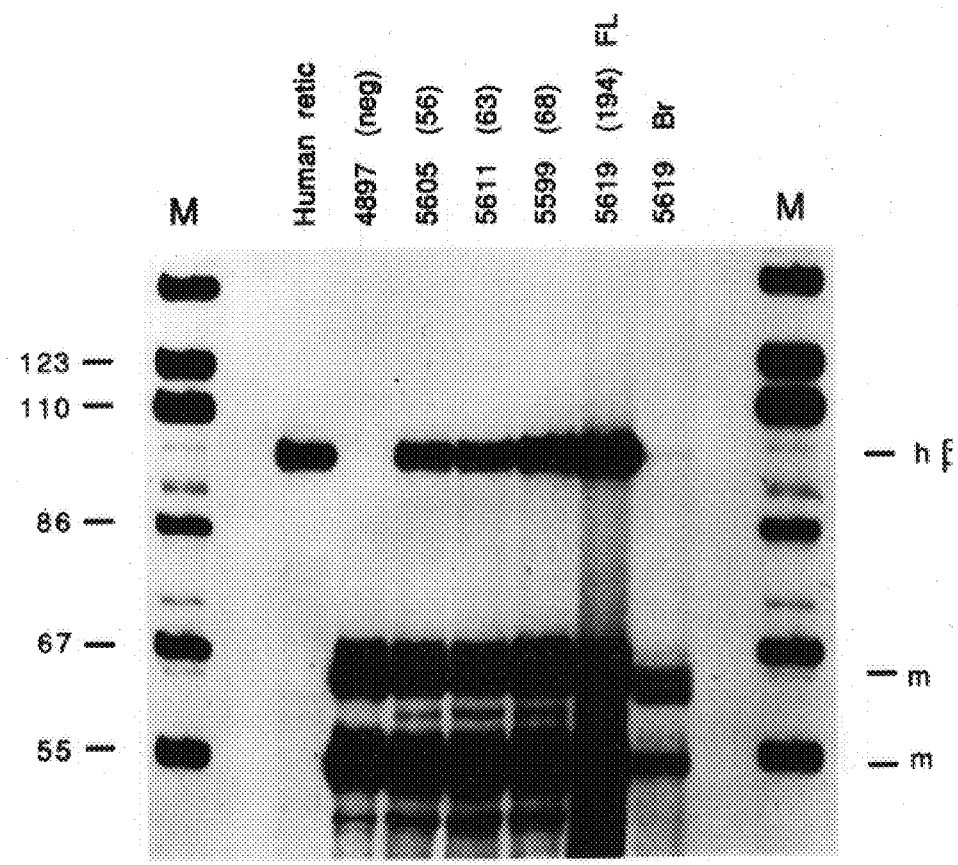

FIG. 13. Primer extension analysis of fetal liver RNA from HS II (1.9) β transgenic mice. As described in the legend to FIG. 8, 5 μg of fetal liver RNA was analyzed. Five micrograms of both fetal liver and brain RNA were analyzed for sample 5619.

Figure 14:
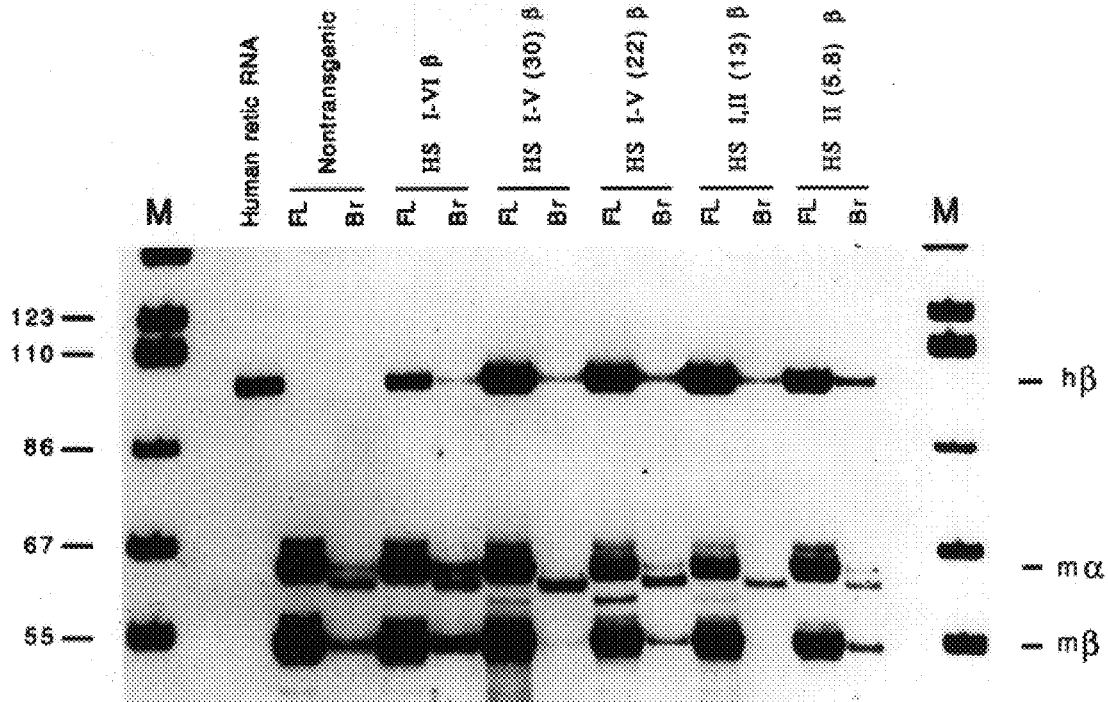

FIG. 14. Primer extension analysis of fetal liver and brain RNA of HS β transgenic mice. As described in the legend to FIG. 8, 5 μg of fetal liver and brain RNA from the highest expresser of each set of HS β transgenic mice were analyzed. The lower level of human β globin mRNA observed in the brain is the result of blood contamination because equivalent levels of mouse α- and β-globin mRNAs are also observed in this tissue.

Figure 15:
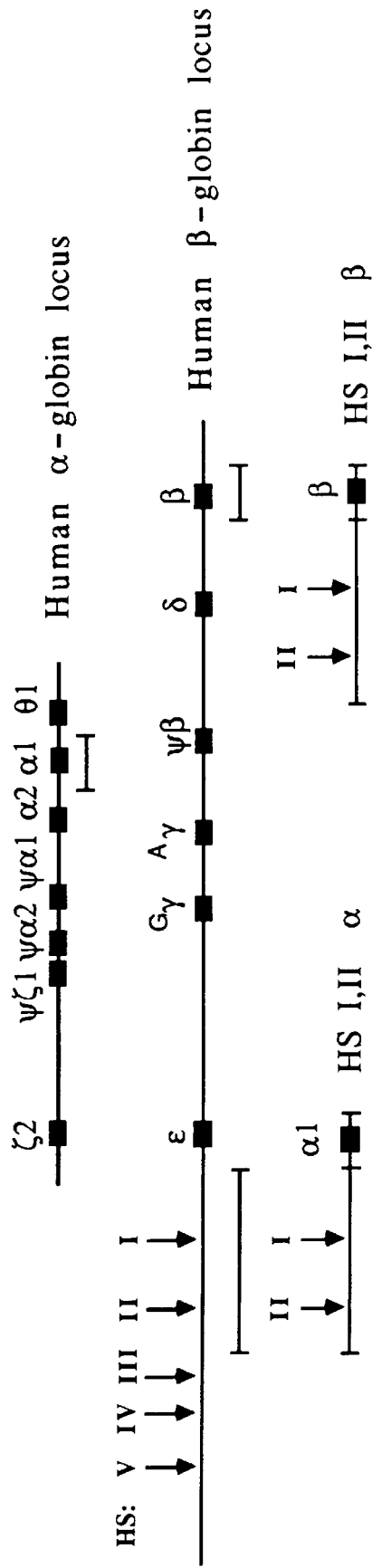

FIG. 15. HS I, II α-globin and HS I, II β-globin gene constructs. Eighty-five kilobases of the human β-globin locus and 35 kb of the human a-globin locus are drawn to scale. The brackets beneath the HS sites, α1-globin gene, and β-globin gene indicate fragments used for construction.

Figure 16A:
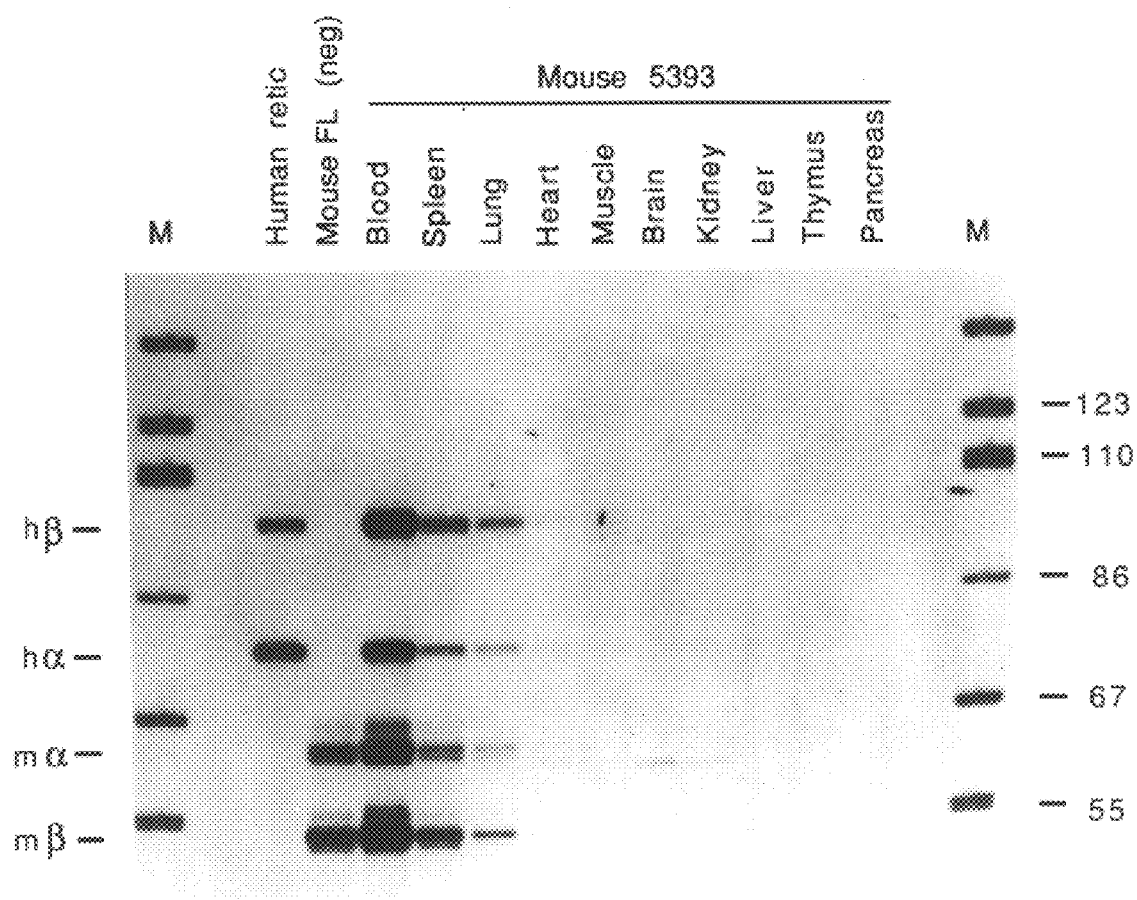
Figure 16B:
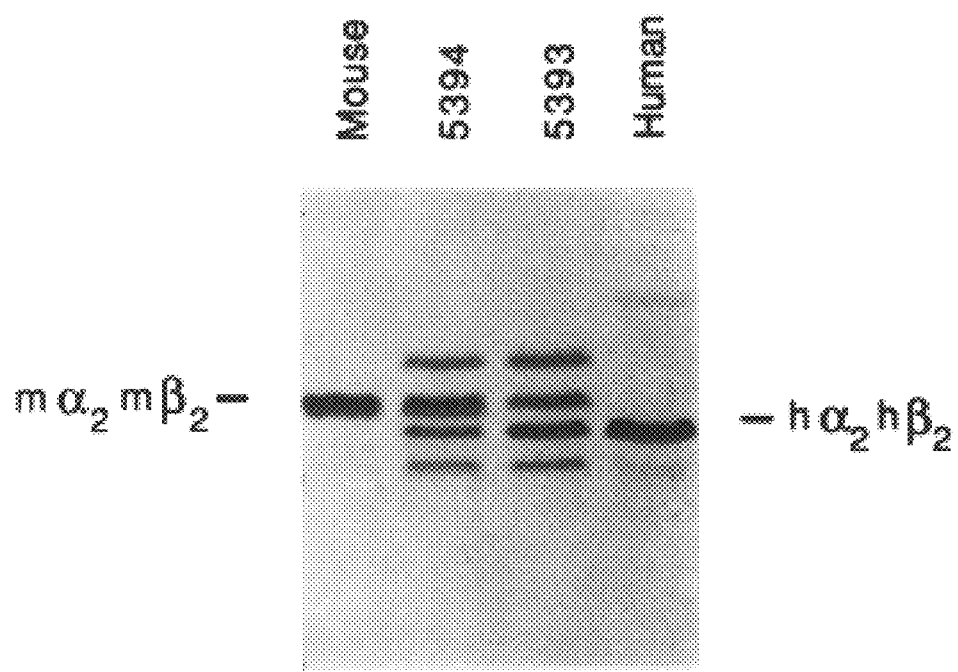

FIG. 16A, 16B. Expression of human α- and β-globin genes in transgenic mice. (A) Primer extension analysis of total RNA from ten tissues of an HS I, II α-globin/HS I, II β-globin transgenic mouse. Human reticulocyte and mouse fetal liver RNAs are controls. Authentic human β- and α-globin primer extension products are 98 bp and 78 bp, respectively, correct mouse α and β globin products are 65 and 53 bp, respectively. Human a and β-globin mRNA detected in lung is the result of incomplete perfusion. Mouse α and β-globin mRNA are also are observed in this non-erythroid tissue. (B) Nondenaturing, isoelectric focusing of transgenic mouse hemolysates. Hemolysates of control mouse (lane 1) human (lane 4) and transgenic mouse (lanes 2 and 3) blood were run on a native agarose isoelectric focusing gel and photographed without staining. (C) Denaturing cellulose acetate strip electrophoresis of transgenic mouse hemogobins. Hemoglobins were denatured in alkaline-urea buffer, electrophoresed on cellulose acetate strips, and stained with imido black. Lanes marked mouse, human, and 5393 are hemolysates of control mouse, human, and transgenic mouse (5393) blood, respectively. Lanes marked 1 to 4 are hemoglobin purified from individual bands (numbered 1 to 4 from top to bottom) of sample 5393 on the isoelectric, focusing gel in (B).

Figure 17:
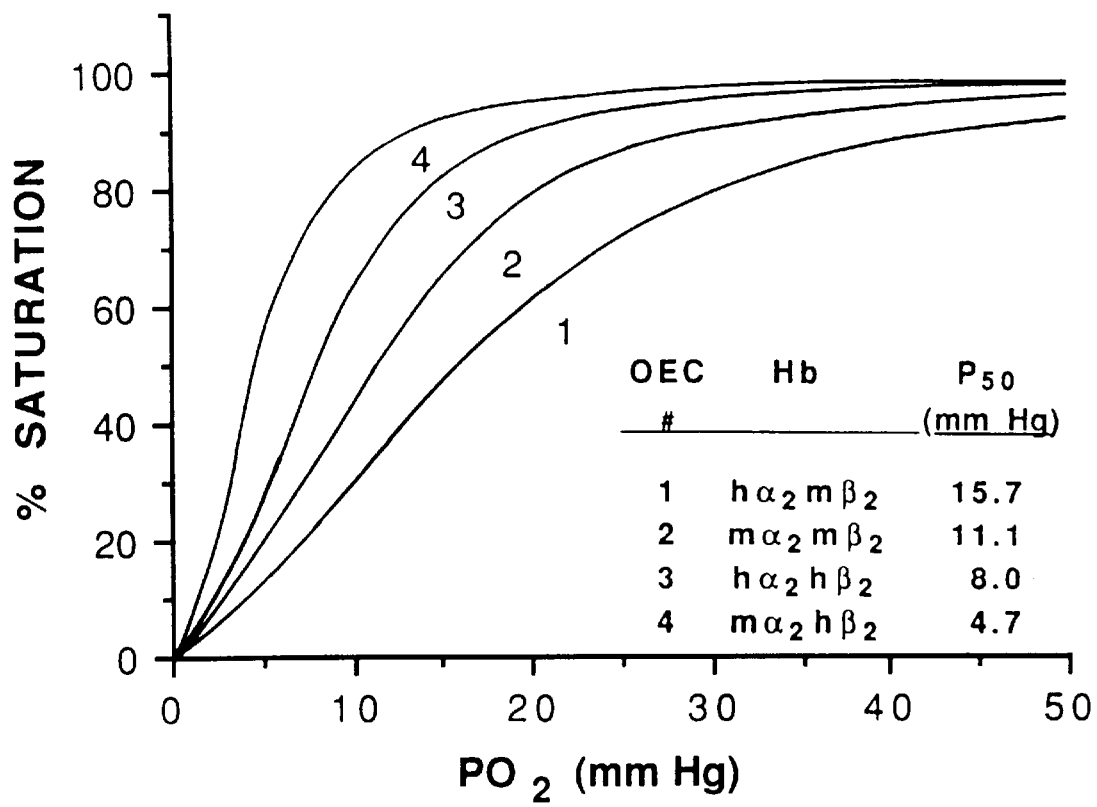
Figure 18A:
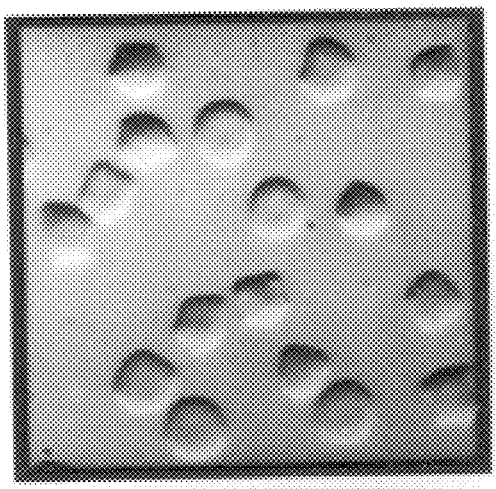
Figure 18B:
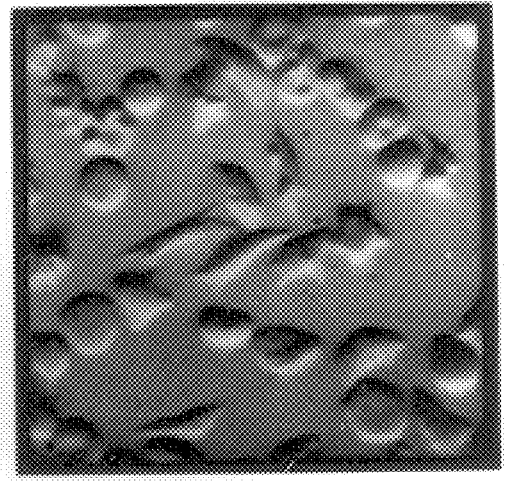
Figure 18C:
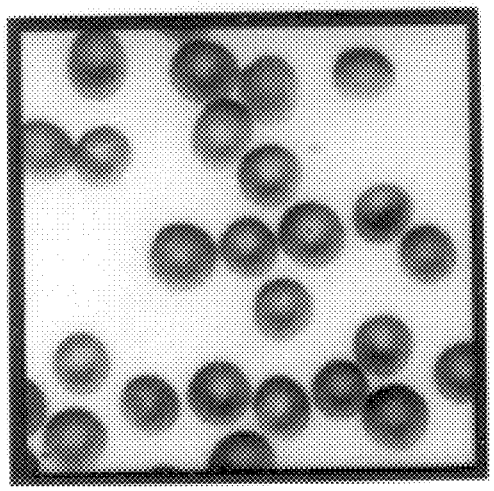
Figure 18D:

FIG. 17. Oxygen equilibrium curves (OEC) of hemoglobins purified from 5393 transgenic mouse progeny. Hemoglobins of 5393 progeny were separated on isoelectric focusing gels. Bands 1 to 4 (top to bottom) illustrated in FIG. 16B were purified from gel slices and the OEC of each hemoglobin band was determined in 0.1M potassium phosphate, pH 7.0 at 20° C. The $P_{50}$ of band 1 ($h\alpha_2\upsilon\beta_2$) is 15.7 mmHg, band 2 ($m\alpha_2\upsilon\beta_2$) is 11.1 mmHg, band 3 ($h\alpha_2\theta\beta_2$); is 8.0 mmHg, and band 4 ($m\alpha_2\theta\beta_2$) is 4.7 mmHg. The $P_{50}$ of human hemoglobin in these transgenic mice is identical to the $P_{50}$ of native human HbA.

FIG. 18. Effect of in vitro deoxygenation on human sickle hemoglobin in human (i) and transgenic mouse (ii) red blood cells.

Figure 19:
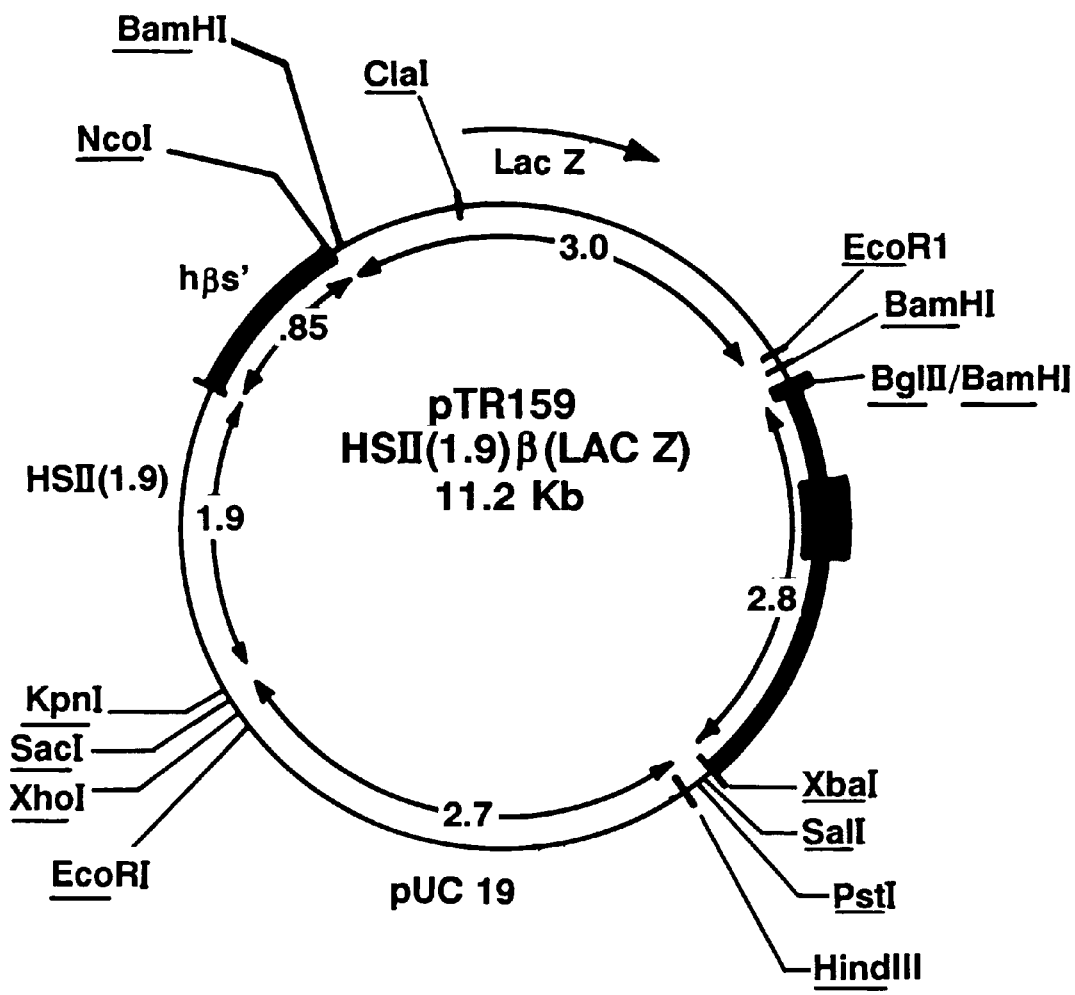

FIG. 19. Recombinant nucleic acid vector for lac Z expression, pTR159, comprising HS II and the lac Z protein coding sequence flanked by sequences from the β-globin locus.

Figure 20:
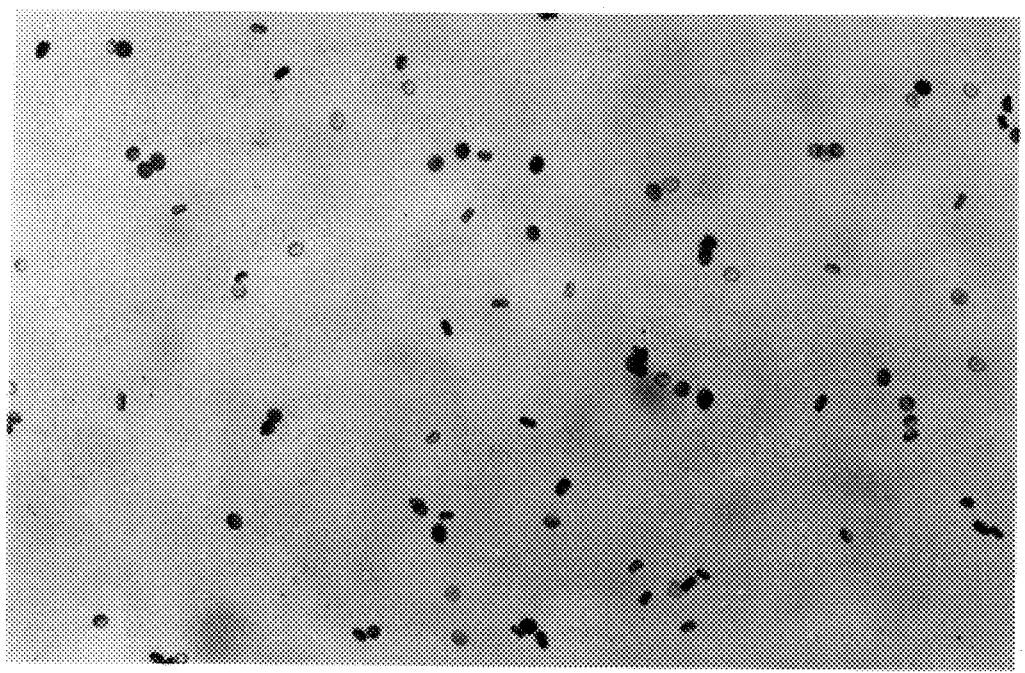

FIG. 20. Expression of lac Z protein in erythrocytes of transgenic mice that carry pTR159. In the presence of the chromogenic substrate X-GAL, a blue color is produced.

Figure 21A:
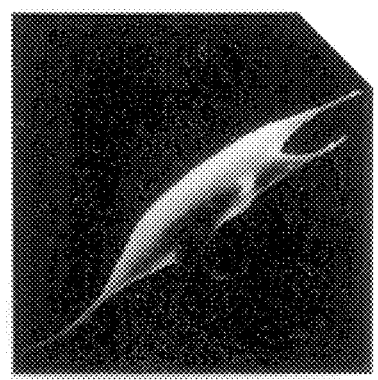
Figure 21B:
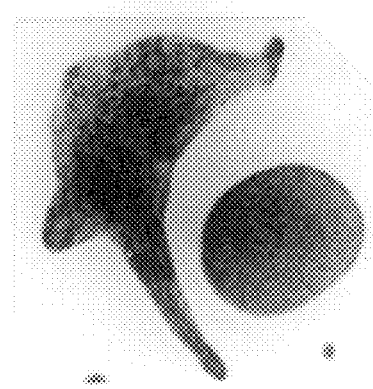
Figure 21C:

FIG. 21A, 21B, 21C. Electron micrograph of sickled cell from transgenic mouse.

5. DETAILED DESCRIPTION OF THE INVENTION

The present invention relates to the synthesis of hemoglobin as well as other useful proteins in erythroid cells of transgenic non-human animals or in cell culture. For purposes of clarity of disclosure, and not by way of limitation, the detailed description of the invention will be divided into the following sections:

(i) Globin genes and recombinant vectors;
(ii) Generation of transgenic animals;
(iii) Transformation of cell lines;
(iv) Expression of proteins in erythroid cells and harvesting of protein; and
(v) utility of the invention.

5.1. Globin Genes and Recombinant Vectors

According to the invention, recombinant DNA molecules may be constructed which comprise at least one of the DNase I hypersensitivity sites found upstream of the β-globin locus together with a gene of interest; introduction of these recombinant DNA molecules into erythroid cells, either in the context of a transgenic animal or in cell culture, will result in high level expression of the gene of interest. In a particular embodiment of the invention, two or more species of such recombinant DNA molecules bearing different genes of interest may be cointroduced into cells in culture or into a transgenic animal in order to produce a protein comprising multiple, distinct subunit proteins, each of which corresponds to one of the species of recombinant DNA molecules introduced. In particular, according to the invention, a protein of interest having more than one species of subunit may be produced in erythroid tissue by a method comprising (i) introducing into erythroid cells (as transgenes in a transgenic animal or as DNA transfected into an erythroid cell line) more than one recombinant nucleic acid construct, each of which comprises a gene encoding a subunit of the protein of interest and at least one erythroid-specific DNase I hypersensitive site; (ii) growing the cells under conditions in which erythroid-specific gene expression occurs (in the transgenic animal this may generally involve normal hematopoiesis, whereas in cell lines it may involve induction of differentiation); and (iii) harvesting the protein of interest from the erythroid cells (such as the red blood cells of the transgenic animal). In a specific embodiment of the invention, recombinant DNA constructs comprising human α-globin encoding DNA sequences together with at least one DNase I HS site and human β-globin encoding DNA sequences together with at least one DNase I HS site may be cointroduced into a transgenic animal in order to produce human hemoglobin in quantity in the erythroid cells of the transgenic animal. Alternatively, according to the invention, a protein of interest having more than one species of subunit may be produced in erythroid tissues of a transgenic animal generated by a method comprising mating two nonhuman transgenic animals, one of which contains a transgene comprising a gene encoding one subunit of the protein of interest and at least one erythroid-specific DNase I hypersensitive site and the other of which contains a transgene comprising a gene encoding another subunit of the protein of interest and at least one erythroid-specific DNase I hypersensitive site; this method may be repeated as may be necessary to produce an offspring which contains a transgene corresponding to each subunit of the protein of interest. The protein of interest may then be purified from the red blood cells of this offspring. It has been observed that if only one of the human globin genes is expressed at high levels in a transgenic animal according to the invention, that animal may clinically resemble a patient with thalassemia (due to an excess of globin not incorporated into hemoglobin); therefore, to optimize the health of the animals, it is preferable, in the case of hemoglobin, to coinject both α and β globin constructs into the same single celled embryo rather than to assemble the α and β subunits by mating animals bearing separate α or β-globin transgenes. The following subsections describe methods for preparing the recombinant nucleic acid molecules of the invention.

5.1.1. Genes of Interest Which May Be Used According to the Invention

The present invention may be used to express any gene of interest in erythroid cells; such erythroid cells may be part of a transgenic animal or, alternatively, may be grown in cell culture. Genes of interest include, but are not limited to, human as well as nonhuman genes; genes encoding globin proteins, non-globin proteins, enzymes, hormones, cytokines, including, but not limited to, the interleukins or interferons, and growth factors. In a preferred specific embodiment of the invention, the genes of interest include human α and β-globin genes. In another specific embodiment of the invention the gene of interest may be tissue plasminogen activator. In another specific embodiment of the invention, the LDL cholesterol receptor is the gene of interest. In yet another specific embodiment of the invention, exemplified in Section 10, infra, the gene of interest is the lac Z gene. Advantageously, proteins of interest produced and sequestered in red blood cells according to the invention may not affect the physiology of the transgenic animal producing the protein. For example, a transgenic animal producing a hormone in its red blood cells according to the invention, if the hormone is engineered to lack a signal sequence, may not be affected by the hormone because the hormone is sequestered in the animal's red blood cells.

5.1.2. Globin Genes

In preferred embodiments of the invention, α and β-globin genes may be incorporated into recombinant nucleic acid molecules together with at least one β-globin associated DNase I hypersensitivity site and the resulting construct may then be introduced into erythroid cells to produce hemoglobin in quantity. In a preferred specific embodiment of the invention, human α-globin and human β-globin genes may be introduced into a transgenic animal as part of transgenes comprising at least one β-globin DNase I HS site. Alternatively, other members of the α and β-globin gene families may be used according to the invention, including, but not limited to, embryonic globin genes, fetal globin genes, and minor globin genes (for example, δ-globin). Additionally, mutant globin genes may also be utilized according to the invention, including but not limited to globin genes associated with human sickle cell anemia and thalassemia. Introduction of mutant human hemoglobins into non-human transgenic animals can produce useful, accurate animal model systems for hemoglobinopathies. In a preferred specific embodiment of the invention, transgenic animals may be created which express human α-globin and human $β^{-S}$-globin genes and which thereby produce human sickle hemoglobin in quantity; the red blood cells of these transgenic animals have been observed to sickle, and therefore recreate the pathology observed in human sickle cell anemia for the first time in an animal model system (see example Section 9, infra).

Globin genes may be isolated from any of the number of clones containing portions of the α or β-globin locus of humans or other animals which are widely available in the art. Globin genes from patients suffering from hemoglobinopathies may be cloned by preparing a genomic library from DNA harvested from the patient (for example, from leukocytes) using methods known in the art, and then using globin gene probes derived from cloned genes of the normal globin locus (which are widely available) to identify, by hybridization, genomic clones containing globin gene sequences (Benton and Davis, 1977, Science 196:180; Grunstein and Hogness, 1975, Proc. Natl. Acad. Sci. U.S.A. 72:3961–3965). Genomic clones identified in this manner may then be analyzed by restriction mapping and sequencing techniques to potentially identify genes bearing mutations.

5.1.3. DNase I Hypersensitivity Sites

DNase I hypersensitivity sites associated with the β-globin gene locus may be used according to the invention to direct the expression of any gene of interest in erythroid cells. DNase I HS sites derived from nonhuman or human globin genes may be used, as may any DNase I HS site from any erythroid specific gene whatsoever, provided that the DNase I HS site in question results in substantial transcription of the gene in question in erythroid cells. According to the invention, β-globin DNase I HS sites HSI, HS II, HS III, HSIV, HSV, or HSVI, any combination thereof, or any duplication thereof, may be used according to the invention; it appears however, that a single copy of HS I may not be sufficient to effectively boost transcription.

Globin DNase I HS sites may be isolated from any of the cloned regions of the globin clusters widely available to those in the art, or, alternatively, from the following recombinant DNA molecules described herein including HS I-V-α, HS I-V-β, and HSI-V-β$^s$, which have been deposited with the American Type Culture Collection (ATCC) and assigned the accession numbers 40665, 40666 and 40664 respectively. In addition, DNase I HS sites that have been mapped may be obtained using any clone of the globin locus and then using the standard technique of chromosome walking to reach a previously identified DNase I HS site (for example, the DNase I HS sites upstream of the human β-globin locus as depicted in FIG. 5). In addition, new erythroid-specific DNase I hypersensitivity sites may be identified by sensitivity to DNase I digestion (as described in Section 2.1.2, supra) and utilized according to the invention.

The extent of expression of the gene of interest can be controlled by altering the number of DNase I HS sites in the recombinant constructs of the invention. In general, the greater the number of HS sites included, the higher the level of expression of the gene of interest that will result. It has been observed that if human HS sites I and II were used to control the expression of human β-globin genes in transgenic mice, the ratio of human to mouse β-globin was found to be about 1:2; however, if all five HS sites were included, the ratio of human to mouse β-globin was about 1:1.

In particular embodiments of the invention in which a non-hemoglobin gene is to be expressed in the erythroid cells of a transgenic animal, if it appears that a particular protein of interest competes with synthesis of endogenous animal hemoglobin, it may be desirable to include only one or two HS sites in order to protect the animal from hypoxia as a result of low hemoglobin content.

5.1.4. Cloning of the Recombinant DNA Molecules of the Invention

DNA reaction products may be cloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript® (Stratagene) plasmid derivatives. Recombinant molecules can be introduced into host cells via transformation, transfection, infection, electroporation, etc.

The gene of interest and at least one globin HS site may be inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endonuclease cleavage sites into the oligonucleotide primers used in polymerase chain reaction to facilitate insertion into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and gene of interest may be modified by homopolymeric tailing.

In addition, in particular embodiments of the invention, the recombinant nucleic acid molecule of the invention may be inserted into any viral vector capable of infecting erythroid cells, including but not limited to retroviruses and Friend Virus A, provided that the dominant element controlling transcription of the gene of interest is the erythroid-specific HS site.

In addition to the DNase I HS site or sites, it may be desirable to incorporate other regions of the β-globin locus into the recombinant nucleic acid vectors of the invention. For example, and not by way of limitation, a recombinant nucleic acid construct may be designed to comprise (i) the protein-coding sequence of a gene of interest, (ii) one or more DNase I HS sites and the β-globin promoter region upstream of the translation initiation site of the gene of interest and (iii) β-globin enhancers downstream of the translation termination site. In a specific embodiment of the invention, and by way of illustration, the HS IIβ/lac Z/β plasmid (FIG. 19) comprises the β-globin HS II DNase I hypersensitivity site and a portion of the β-globin locus including the β-globin promoter upstream of the translational initiation site of the lac Z gene; downstream of the translational stop codon, the plasmid comprises a portion of the β-globin locus which includes the enhancer found in the second intron of the β-globin gene as well as part of the third exon of β-globin and the enhancer located 3' to the human β-globin gene.

Provided an erythroid-specific DNase I HS site is included, the recombinant nucleic acid vectors of the invention may include any transcriptional promoter known in the art, including but not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpesvirus thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, 1985, Mol. Cell. Biol. 5:1639–1648; Hammer et al., 1987, Science 235:53–58); alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340, Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

5.2. Generation of Transgenic Animals

The recombinant DNA molecules of the invention may be introduced into the genome of non-human animals using any method for generating transgenic animals known in the art.

In general, the scheme presently employed to produce transgenic mice involves the following: male and female mice, from a defined inbred genetic background, are mated at midnight. Twelve hours later, the female is sacrificed and the fertilized eggs are removed from the uterine tubes. At this time, the pronuclei have not yet fused and it is possible to visualize them in the light microscope. Foreign DNA is then microinjected (100–1000 molecules per egg) into a pronucleus. Shortly thereafter fusion of the pronuclei (a female pronucleus or the male pronucleus) occurs and, in some cases, foreign DNA inserts into (usually) one chromosome of the fertilized egg or zygote. The zygote is then implanted into a pseudo-pregnant female mouse (previously mated with a vasectomized male) where the embryo develops for the full gestation period of 20–21 days. The surrogate mother delivers these mice and by four weeks the pups are weaned from the mother. To test these mice for the presence of foreign DNA, a portion of the tail (a dispensable organ) is removed and the DNA extracted. DNA—DNA hybridization (in a dot blot, slot blot or Southern blot test) is employed to determine whether the mice carry the foreign DNA. Of the eggs injected, on average 10% develop properly and produce mice. Of the mice born, on average one in four (25%) are transgenic for an overall efficiency of 2.5%. Once these mice are bred they pass along the foreign gene in a normal (Mendelian) fashion linked to a mouse chromosome. Mating two homozygous mice with the transgenic DNA means 100% of the offspring carry two copies of the transgene.

When this is done it is common that the mice carry tandemly repeated copies of the foreign gene (from 3–80 copies) at one chromosomal location or site.

The present invention is not limited to any one species of animal, but provides for any non-human animal species which may be appropriate. For example, mice, guinea pigs, rabbits and pigs, sheep, cows, goats, and horses, to name but a few, may provide useful transgenic systems.

Likewise, any method known in the art may be used to produce transgenic animals, including but not limited to, microinjection, cell gun, transfection of DNA, and electroporation.

It is preferable to remove prokaryotic sequences from eukaryotic sequences prior to the introduction of eukaryotic sequences into the single-celled embryos, using techniques (e.g. gel electrophoresis known in the art.

5.3. Transformation of Cell Lines

Transfection of cell lines may be performed by the DEA dextran method (McCutchen and Pagano, 1968, J. Natl. cancer Instit. 41:351–357), the calcium phosphate procedure (Graham et al., 1973, J. Virol. 33:739–748) or by any other method known in the art, including, but not limited to, microinjection, lipofection, and electroporation.

5.4. Expression of Proteins in Erythroid Cells and Harvesting of Protein

The recombinant molecules of the invention may be used to result in expression of the gene of interest in erythroid cells due to the presence of the erythroid-specific DNase I HS sites.

In a preferred embodiment of the invention, the recombinant molecules of the invention may be used to produce a gene of interest in the erythroid cells of a non-human transgenic animal. According to the present invention, red blood cells may be harvested from said transgenic animal, and the protein product of the gene of interest may be harvested by lysing the cells and purifying the desired protein product using methods known in the art, including, but not limited to chromatography (e.g., ion exchange, affinity, and sizing column chromatography), centrifugation, differential solubility, electrophoresis, or any other standard technique for the purification of proteins.

In a specific embodiment of the invention, human hemoglobin may be harvested from the blood of transgenic non-human animals carrying $\alpha$ and $\beta$-globin transgenes and DNase I HS sites by hemolyzing the blood and separating proteins by nondenaturing isoelectric focusing according to the following method:

Blood cells may be washed several times with saline and then lysed in a volume of water equal to the cell pellet; one-fourth volume of carbon tetrachloride may then be mixed with the hemolysate, and cell membranes may be extracted by brief vortexing and microcentrifugation. The aqueous phase may then be removed and frozen at 20° C. Samples may be subsequently thawed, diluted with an equal volume of 0.05% KCN, and separated on an agarose isoelectric focusing gel (Re solve-Hb, Isolabs Inc., Akron, Ohio) according to the manufacturer's specifications. After focusing, proteins may be fixed in the gel with 10% trichloroacetic acid for 10 minutes. The gel may then be rinsed with water, dried, and hemoglobin bands visualized without staining. Human hemoglobin may be visualized as a distinct band, and may be identified by running a standard preparation of human hemoglobin alongside the transgenic hemoglobin sample. Human hemoglobin bands may be cut from the gel. The above method may be scaled up appropriately using methods known in the art, and may be modified for chromatographic separation.

Blood may be harvested from the transgenic animals of the invention using any humane method known in the art. It may be advantageous to draw small quantities, preferably between about 5 to 7.5 percent of the animals total blood volume, at regular intervals. To minimize the animals discomfort, an indwelling venous catheter may be inserted such that blood may be drawn easily, safely, and painlessly and with a minimum of veterinary skill. It may be desirable to utilize transgenic animals which have a large blood volume, including but not limited to, cows and horses.

Importantly, any method known in the art may be used to increase red blood cell formation in the transgenic animals of the invention, provided that it does not result in unreasonable discomfort for the animals, including, but not limited to, the administration of erythroipoietin or the maintenance of animals at partial pressures of oxygen comparable to those found at high altitudes.

Similarly, the recombinant molecules of the invention may be incorporated into erythroid cell lines, and subsequently harvested. It may be necessary to transform the cells, using any method known in the art (see Section 5.3, supra) while the cells are in a relatively undifferentiated state, and then to induce the cells to differentiate and subsequently harvest the gene product of interest. For example, and not by way of limitation, the recombinant molecules of the invention may be transfected into murine erythroleukemia cells which may then be induced to differentiate (e.g. using dimethylsulfoxide); the gene product of interest may then be harvested by lysing the cells and purifying the gene product of interest using standard protein purification techniques.

5.5. Utility of the Invention

The foremost advantage of the invention lies in the utilization of red blood cells to efficiently manufacture, in quantity, gene products of interest. Virtually no other cell in the body is devoted to the synthesis of a single protein product to the extent that erythroid cells are committed to the synthesis of hemoglobin. The developing red blood cell down-regulates the expression of the vast majority of its genes in order to focus its synthetic machinery on the production of hemoglobin; in doing so it loses its nucleus and most other organelles and becomes, essentially, a membrane-bound packet of hemoglobin. The domination of the red cell's synthetic capabilities is effected, to a large extent, by a formidable surge of transcription of globin genes upon commitment to differentiation. By redirecting the red cell transcriptional signals toward inducing expression of a gene of interest by attaching it to a globin HS site, the present invention exploits the genetic programming of erythroid cells and thereby provides a surpassingly efficient method for producing a gene of interest in quantity and at a purity superior to that which would be found in the majority of cell extracts.

A recombinant vector comprising the HS II site and the lac Z gene has been constructed (FIG. 19) which was observed to direct high levels of lac Z expression in erythroid cells of transgenic mice, as detected by its ability to cleave the chromogenic substrate X-gal (FIG. 20, see Section 10, infra).

Human hemoglobin produced according to the invention can be used as a non-immunogenic, pathogen-free red blood cell substitute which may be used to transfuse human patients in need of such treatment. Advantageously, because the human hemoglobin produced according to the invention is free of cell surface antigens, it may be used as a red blood cell substitute in patients of any and all known blood types.

5.5.1. Transgenic Animal Models For Hemoglobinopathies

Transgenic non-human animals carrying human α- and β-globin genes in which one or both transgenes are mutated relative to the wild-type human gene, may be used as model systems for human diseases, including, but not limited to, sickle cell disease and thalassemia. Section 9, infra describes the development of a transgenic mouse which expresses the human α-globin and $\beta^S$-globin (sickle cell hemoglobin) genes; the red cells of these mice have been observed to assume a sickle configuration when deoxygenated in vitro. Importantly, other investigations have expressed only the human $\beta^S$-globin gene in transgenic mice; the red blood cells of these mice, produce a chimeric hemoglobin in which human $\beta^S$-globin complexes with murine α-globin; the red cells of these transgenic mice do not sickle in response to deoxygenation (Rubin et al., 1988, J. Clin. Invest. 82:1129–1133; Rubin et al., 1988, Am. J. Hum. Genet. 42:585–591).

5.5.2. Vectors of the Invention in Gene Therapy

In a further embodiment, the recombinant molecules of the invention may be used as instruments of gene therapy in genetic diseases affecting erythroid tissues, including, but not limited to, sickle cell disease and thalassemia. For example, the constructs of the invention, comprising a globin gene and one, or preferably more than one, HS sites, may be introduced into the bone marrow cells of a patient in need of such treatment who suffers from defective or absent expression of that globin gene; the constructs of the invention may be used to reconstitute the patient's hemoglobin to a physiologically normal form. In various embodiments of the invention, the gene is introduced by a retroviral vector. In specific embodiments, human γ or β-globin genes under the transcriptional control of HS sites may be inserted into erythroid cells by a retroviral vector; human γ globin may prove advantageous for preventing hemoglobin sickling. It has been known, clinically, that 15–20% fetal hemoglobin ($\alpha_2\gamma_2$) expression in sickle-cell patients or patients with β-thalassemia ameliorates the disease.

In a further specific embodiment of the invention, a retroviral vector comprising at least one erythroid-specific DNase I HS site and the gene encoding the human low density lipoprotein (LDL) receptor may be introduced into the bone marrow of a patient suffering from high cholesterol; the red blood cells which develop from stem cells in the bone marrow may exhibit LDL receptors on their surfaces, and may advantageously decrease the serum cholesterol in the patient.

6. EXAMPLE

High-Level Erythroid Expression of Human α-Globin Genes In Transgenic Mice

6.1. Materials and Methods

6.1.1. α-GLOBIN AND HS I, II α-GLOBIN CONSTRUCTS

The α-globin gene was originally obtained as a 3.8-kb BglII-EcoRI fragmented inserted into BamHI and EcoRI sites of pBR322 (Lauer et al., 1980, Cell 20:119–130). The EcoRI site was changed to a SalI site, and a 3.8-kb XhoII-SalI fragment was subcloned into the BamHI and SalI sites of a modified pUC19 plasmid. The modified plasmid contained ClaI and MluI sites immediately upstream of the BamHI site. A 12.9-kb MluI-ClaI fragment containing HS sites I and II was obtained from λ5εII (Li et al., 1985, J. Biol. Chem. 5260:14901–14910) and was inserted into the MluI and ClaI sites of the modified plasmid to produce HS I, II α.

6.1.2. Sample Preparation and Microinjection

A 3.8 kb XhoII-EcoRI fragment containing α-globin alone and a 16.7-kb MluI-SalI fragment containing HS I, II α-globin were isolated from 1.0% low-gelling-temperature agarose (FMC) gels, extracted twice with phenol (buffered with 0.1 M Tris-HCl, pH 8.0/1.0 mM EDTA), extracted once with phenol/chloroform, extracted once with chloroform, and then precipitated with ethanol. After resuspension in TE (10 mM Tris-HCl, pH 8.0/1.0 mM EDTA), the fragments were again extracted sequentially with phenol, phenol/chloroform, and chloroform and then precipitated with ethanol. The purified fragments were washed with 70% ethanol, resuspended in sterile TE, and then microinjected into the male pronuclei of $F_2$ hybrid eggs from C57BL/6× SJL parents as described by Brinster et al. (1985, Proc. Natl. Acad. Sci. U.S.A. 82:4438–4442). Embryos were removed at day 16 of gestation, and total nucleic acids were prepared as described.

6.1.3. DNA Analysis

Embryos that contained the injected constructs were determined by DNA dot hybridization of brain nucleic acids with human α-globin and HS II-specific probes that were labeled by extension of random primers (Feinberg et al., 1983, Anal. Biochem. 132:6–13). The human a probe was a 1.5-kb PstI fragment containing the entire human α-globin gene and the HS II probe was a 1.9-kb HindIII fragment spanning the HSII site. Hydbridizations were performed at 68° C. for 16 hr in 5×SSC1×SSC1=0.15 M sodium chloride and 0.015 M sodium citrate, pH 7) 5× Denhardt's (1× Denhardt's=0.02% polyvinylpyrrolidone, 0.02% Ficoll 0.02 bovine serum albumin), 100 μg of herring sperm DNA per ml and 0.1% SDS. Filters were washed three times for 20 min each at 65° C. in 2× SSC/0.1% SDS and for 20 min at 65° C. in 0.2 SSC (if necessary) to reduce background.

For Southern blots, 10 μg of fetal liver DNA from animals that were positive for human α-globin and HS I, II α-globin were digested with PstI or PvuII, electrophoresed on 1.0% agarose gels, blotted onto nitrocellulose, and hybridized with the a and HS II probes described above. The hybridization conditions for Southern blots were the same as those described for DNA dots.

6.1.4. RNA Analysis

RNA was prepared from total nucleic acids by digesting the sample with DNase I (Worthington, RNase-free) at 10 μg ml for 20 min at 37° C. in 10 mM Tris-HCl, pH 7.5, 10 mM MgCl, and 50 mM NaCl. The reaction was stopped with EDTA, and the sample was digested with proteinase K (100 μg ml) for 15 min at 37° C. After digestion, RNA was purified by phenol chloroform and chloroform extraction, precipitated with ethanol and resuspended in TE.

Quantitation of human α and mouse β-globin oligonucleotide 5'-CGACGACAGAGACCGGACACC-3' corresponds to sequences from +80 to +100 of the $\beta^r$ and $\beta^s$-globin genes, which are identical in this region. The human a oligonucleotide 5 GGCCTTGACGTTGGTCTTGTCGGCAGG-3' corresponds to sequences from +50 to +76 of the human α1-globin gene.

Primer extensions were performed as described by Townes et al. (1985, EMBO J. 4:1715–1723) except that only 5 μg of fetal liver or brain RNA was analyzed and three oligonucleotides were used in each reaction. The human a primer was the same as the one used for solution hybridizations. The mouse a primer 5'-CAGGCAGCCTTGATGTTGCTT-3' corresponds to sequences from +45 to +65 of the mouse α1- and α2-globin genes, which are identical in this region. The mouse β primer 5-TGATGTCTGTTTCTGGGGTTGTG-3' corresponds to sequences from +31 to +53 of the mouse $\beta^s$ globin gene. Although there is a two-basepair difference in the $\beta^s$ and $\beta^r$-genes in the region covered by this oligonucleotide, comparision of solution hybridization results with primer extension data suggest that the primer anneals with equal efficiency to $\beta^s$- and $\beta^r$ globin mRNA under the hybridization conditions used.

6.2. Results

6.2.1. Production of Human α-Globin and HS I,II α-Globin Transgenic Mice

FIG. 1 illustrates the human α and β-globin loci and the two DNA fragments (α and HS I, II α) that were injected into fertilized mouse eggs. The α-globin gene is contained on a 3.8-kb BglII-EcoRI fragment that has about 1.3kb of 5' flanking and 1.5 kb of 3' flanking sequence. HS I, II a was constructed by inserting a 12.9-kb MluI-ClaI fragment containing DNase I HS sites I and II from the human β-globin locus upstream of the α1-globin gene. Each construct was purified from vector sequences and injected into fertilized eggs. These eggs were transferred into the uteri of pseudopregnant foster mothers, and after 16 days of deveopment the embryos were removed. Total nucleic acids were prepared from fetal livers and brains, and DNA dots were analyzed with α-globin specific and HS II-specific probes. Twelve embryos containing HSI, II α-globin and four embryos containing α-globin alone were obtained. These DNA-positive samples were then analyzed by Southern blotting to examine the integrity of the transgenes and to determine copy number. When the samples were cut with PstI and probed with the α-globin probe, a single 1.5-kb band was observed (FIG. 2A). This fragment contains the entire α1-globin sequence plus 570 have pairs of 5' flanking and 92 base pairs of 3' flanking sequence. Lanes 1–3 of FIG. 2a are herring sperm DNA spiked with the equivalent of 25, 2.5, and 0.25 copies per cell of the α1-globin construct; lane 4 is human DNA, and lane 5 is a nontransgenic mouse control. All of the α and HS I, II α transgenic fetuses contained intact copies of the α-globin gene at 0.25–15 copies per cell. Samples containing HS I, II α-globin were also cut with PvuII and probed with the HS II probe to determine transgene integrity (FIG. 2B). A 6.9-kb band that contains HS I is observed in all samples. In addition, all of the samples except one (5058) have a 5.2-kb band that contains HSII and spans the junctions of head-to-tail tandem repeats (see FIG. 2C). The data from these Southern blots demonstrate that all of the HS I, II α animals except one contain intact copies of the transgene. The single animal that lacks the 5.2 kb band appears to have lost the HS II site but has maintained HS I. Animals that have the 5.2 kb band but contain less than one copy per cell of the transgene are mosaics. These animals contain at least two head-to-tail tandem repeats, but the injected fragments are present in less than one out of two to four cells.

6.2.2. Expression of Human α-Globin mRNA in HS I, II α Transgenic Mice

Mice switch directly from embryonic to adult hemoglobin synthesis when fetal liver becomes the major site of erythropoeisis at 13–17 days of development. Therefore, we analzyed 16-day fetal liver RNA from α and HS I,II α transgenic animals for correctly initiated human α-globin, mouse α-globin, and mouse β-globin mRNA by primer extension. The results of this experiment are illustrated in FIG. 3. No human α-globin mRNA could be detected in the 4 transgenic mice containing the α-globin gene alone or in the one animal that had lost the HS II site. However, all II transgenic mice that contained intact copies of HS I, II α-globin expressed correctly initiated human α-globin mRNA. Accurate quantitative values of human α-globin and mouse β-gloin mRNA levels were determined by solution hybridization with human α-specific and mouse β-specific oligonucleotides. No human α-globin mRNA could be detected in a transgenic animals or in the one HS II-minus mouse at a sensitivity of 0.2% of endogenous mouse β-globin mRNA. However, mice that contained intact copies of HS I, II α expressed human α-globin mRNA at levels ranging from 4% to 337% of mouse β-globin mRNA levels. (Table I). Although the highest levels of expression were observed in animals that contained higher levels of expression were observed in animals that contained higher copy numbers of the transgene, there was not an absolute correlation between copy number and expression. When human α-globin and mouse β-globin mRNA levels were calculated per gene copy, human α-globin values ranged from 28.8% to 90.0% of endogenous mouse β-globin levels. This high level of expression may be even higher when calculated on a per cell basis because some of these animals are mosaics. Expression was originally calculated as a percentage of mouse β-globin mRNA instead of mouse β-globin mRNA in case the endogneous mouse α-globin gene was down-regulated. However, the primer extensions in FIG. 3 and subsequent solution hybridizations with a mouse α-globin-specific oligonucleotide demonstrate that mouse α-globin is not consistently down-regulated even in high expressors and that mouse α and β-globin mRNA levels are essentially equivalent.

sequences essential for normal α-globin expression have been missing in the constructs tested so far. The only successful instances of correctly regulated α-globin gene expression outside of human erythroid cells have been in somatic cell hybrids (Charney, et al., 1984 supra) or heterokaryons (Baron et al.,1986, Cell 46:591–602) formed between erythroid or nonerythroid human cells and MEL cells in culture. In both of these instances, complete human chromosomes were transferred to mouse cells. Therefore,

TABLE I

Quantitation of HS I, II α Expression

| Parameter | Mouse | | | | | | | | | | |
|---|---|---|---|---|---|---|---|---|---|---|---|
| | 5039 | 5034 | 5041 | 5067 | 5052 | 5055 | 5040 | 5042 | 5064 | 5050 | 5054 |
| $\frac{h\alpha\ mRNA}{m\beta\ mRNA} \times 100$ | 4.0 | 10.3 | 8.4 | 14.9 | 18.0 | 41.2 | 55.0 | 72.0 | 225.0 | 156.0 | 337.0 |
| hα gene copies/cell | 0.25 | 0.50 | 0.50 | 2.0 | 4.0 | 5.0 | 7.0 | 10.0 | 10.0 | 15.0 | 15.0 |
| $\frac{h\alpha\ mRNA/h\alpha\ gene}{m\beta\ mRNA/m\beta\ gene} \times 100$ | 64.0 | 82.0 | 67.2 | 29.8 | 72.0 | 32.8 | 31.6 | 28.8 | 90.0 | 41.6 | 90.0 |

Human (h) α-globin and mouse (tmr) β-globin mRNA levels were quantitated by solution hybridization with human α-globin and mouse β-globin specific oligonucleotides as described (Townes et al., 1985, EMBO J. 4:1715–1723). The number of copies of HS I, II α per cell was determined by densitometric scanning of the Southern blot illustrated in FIG. 2A. The values of percent expression per gene copy in the bottom row were calculated assuming four mouse β-globin genes per cell. The C57BL/SJL mice used in this study have the Hbb$^s$ or single haplotype. The β-globin locus in this haplotype contains two adult β-globin genes (β$^s$ and β$^2$) per haploid genome C57BL/SJL mice also have two α-globin genes (α1 and α2) per haploid genome.

6.2.3. Tissue Specificity of HS I, II α Trangene Expression

Fetal liver and brain RNA from the three highest HS I, II αexpressors (5064, 5050 and 5054) were analyzed by primer extension for human α-globin, mouse α-globin, and mouse β-globin mRNA to assess the tissue specificity of human α-globin gene expression under the influence of hypersensitive sites I and II. Data in FIG. 4 demonstrate that the human α-globin gene is expressed at high levels in fetal liver but not in brain. The small amount of human a globin mRNA in the brain results from blood contamination because equivalent amounts of mouse α-globin and β-globin mRNA are also observed in this nonerythroid tissue. These data strongly suggest that hypersensitive sizes I and II act specifically in erythroid tissue to stimulate human α-globin gene expression in transgenic mice.

6.3. Discussion

Correctly regulated expression of human α-globin genes has previously been difficult to achieve in any functional assay system. The α globin gene is transcribed at high levels in nonerythroid culture cells even in the absence of viral enchancer sequences (Treisman et al., 1983, Proc. Natl. Acad. Sci. U.S.A. 80:7428–7432; Charney, et al., 1984, Cell 38:251–263). When human α-globin genes are introduced into murine erythroleukemia (MEL) cells, high-level constitutive expression is observed (Charney, et al., 1984, Cell 38:251–263). In several experiments, expression was even shown to decrease in induced MEL cells (Charney, et al., 301984, Cell 38:251–263). In contrast, the human α-globin gene is not expressed at all when introduced into mice (Palmiter, et al., 1986, Annu. Rev. Genet. 20:465–499). Even cosmid fragments that contain the entire human α-globin locus are not expressed. These observations suggest that sequences that normally activate the human α-globin locus may be located very far upstream of β-globin or downstream of α-globin.

The results described above demonstrate that high levels of human α-globin gene expression can be obtained in erythroid tissue of transgenic mice when DNase I HS sites I and II from the human β-globin locus are inserted upstream of the gene. mRNA levels as high as 337% of endogenous mouse β-globin mRNA levels were obtained in fetal liver, and no expression was observed in fetal brain. These results demonstrate that the erythroid-specific HS sites activate human α-globin gene in erythroid tissue regardless of the site of transgene integration. The single animal (5058) that contained HS I but not HS II did not express α-globin mRNA. This result suggests that HSI is not sufficient to direct α-globin gene expression. Future experiments will determine whether HS II in sufficient to enhance expression of if HS I and II cooperate to stimulate high levels of globin gene expression in transgenic mice. We have also demonstrated that HSI and II cooperate and are sufficient to stimulate high levels of globin gene expression in transgenic mice. The results presented here demonstrate that the activity of HS I and II is not limited to β-globin genes.

High-level expression of human α-globin genes in transgenic mice now provides the opportunity to produce a complete functional human hemoglobin in a mouse. In addition, coexpression of human α-globin and mutant β-globin genes in transgenic mice may provide important models for human hemoglobinopathies. A mouse model for sickle cell disease would be especially valuable. Expression of the β-globin gene alone in transgenic mice is not sufficient for sickling because hybrid tetramers formed between mouse α-globin and human β-globin polypeptides do not polymerize (Rhoda, M. D. Domenget, C., Vidaud, M., Bardakdian-Michau, J. Rouyer-Fessard, P., Rosa, J. &

Beuzard, Y. (1988: Biochim. Biophys. Aeta 952, 208–212). Therefore, high-level coexpression of human α- and β-globin genes will be required to produce sickling red blood cells (Ryan et al., 1989, Proc. Natl. Acad. Sci. U.S.A. 86:37–41, which is incorporated by reference in its entirety herein.

7. EXAMPLE

A Single Erythroid-Specific DNase I Super-Hypersensititve Site Activates High Levels of Human β-Globin Gene Expression In Transgenic Mice

7.1. Materials and Methods

7.1.1. Construction of HS β-Globin Clones

Lambda clones containing HS sites I–IV (5'εII and 5'εIII; Li et al., 1985, J. Biol. Chem. 260:14901–14910) were kindly provided by Oliver Smithies, and a λ clone containing HS (λ4) was kindly provided by Don Fleenor and Russell Kaufman. A 1.9-kb HindIII fragment containing HSIII was prepared from 5'EIII and subcloned into pUC19. A 1.3-kb BamHI-HindIII fragment from this plasmid was then used to screen a human placenta genomic library in EMBL 4 (Stratagene) and several clones that overlapped with 5'εIII were isolated. One clone that contained a 17.5-kb insert extended ~11.0 kb upstream of the EcoRI site at the 5' end of the 5'εIII clone. This new clone, which was designated 5'εIV, contained HS V. Cosmid clone HS I-V (30) β was constructed as follows. A 17-kb SalI-MluI fragment was prepared from 5'εIV; the SalI site was from the EMBL 4 SalI-BamHI cloning site, and the MluI site was a natural site in the insert. This 17-kb fragment contained HS V, HS IV, and HS III. A 13-kb MluI-ClaI fragment containing HS II and HSI was prepared from $^{5'}$εII. These two fragments were inserted into the cosmid vector pCV00I (Lau and Kan, 1983, Proc. Natl. Acad. Sci. U.S.A. 80:5225–5229) in a four-way ligation. The left arm was a 9.0-kb MluI-SalI fragment obtained from pCV001; the MluI site was destroyed by S1 digestion. This fragment contained a cos site, an ampicillin-resistance gene, a ColEI origin, and the SVneo gene. The right arm was a 6.6-kb ClaI-HindIII fragment that contained the human β-globin gene on a 4.1-kb HpaI-XbaI fragment and a cos site from pCV001 on a 2.5-kb SalI-HindIII fragment. The HpaI and XbaI sites on either side of the β-globin gene were changed to ClaI and SalI, respectively, in the right arm plasmid.

These four fragments were ligated in a 2:1:1 vector arms to inserts and packaged (Gigapack Gold; Stratagene). *Escherichia coli* ED8767 was then infected with the packaged cosmids and plated on ampicillin plates. Large-scale cultures of ampicillin-resistant colonies were grown and cosmids were prepared by standard procedures.

The HS I-V (22) β cosmid was constructed as follows. A 12-kb BglII fragment containing HS V, HS IV HS III, and HS II was subcloned from HS I-V (30) β into a modified pUC plasmid, and a 10.7-kb SalI-KpnI fragment containing HS V, HS IV, and HS III was prepared from this plasmid. The SalI site of this fragment was from the pUC polylinker, and the KpnI site was a natural site in the insert. A 10.9-kb KpnI-ClaI fragment containing HS II and HS I was isolated from 5'εII and subcloned into a modified pUC plasmid. The 10.7-kb SalI-KpnI fragment containing HS V, HS IV, and HS III was ligated to the 10.9-kb KpnI-ClaI fragment containing HS II and HS I and the two cosmid vector arms described above. The ligation mixture was packaged, ED8767 cultures were infected, and cosmids were prepared from ampicillin-resistant colonies.

HS I-VI β was prepared as follows. A 12.0-kb HpaI-BamHI fragment containing HS VI was subcloned from λ4 into a modified pUC19 plasmid and then isolated from this plasmid as a 12.0-kb XhoI-SalI fragment. This fragment was cloned into the SalI site downstream of the human β-globin gene in the right-arm plasmid described above. The right-arm plasmid was then linearized with ClaI and dephosphorylated with calf intestinal phosphatase (Boehringer-Mannheim). This 21-kb right-arm fragment and the 9.0-kb SalI-KpnI fragment containing HS V, HS IV, and HS III and the 10.9-kb KpnI-ClaI fragment containing HS II and HS I in a 2:1:1 molar ratio of vector arms to inserts. The ligation mixture was packaged, ED8767 cultures were injected, and cosmids were prepared from ampicillin-resistant colonies.

HS I.II (13) β was derived from HS 1-V (22) β after digestion with MluI and SalI. HS II (5.8) β and HSII (1.9) β were constructed by subcloning the 5.8-kb MluI-BstEII fragments or the 1.9-kb KpnI-PvuII fragment into modified pUC plasmids containing the human β-globin gene.

7.1.2. Sample Preparation and Microinjection

All of the constructs were removed from vector sequences by digestion with the appropriate enzymes and isolated on low-gelling temperature agarose (FMC) gels. Gel slices were melted, extracted twice with phenol (buffered with 0.1 M Tris-HCl (pH 8.0), 1.0 mM EDTA), once with phenol/chloroform, and once with chloroform and precipitated with ethanol. After resuspension in TE (10 mM Tris-Hcl (pH 8.0), 1.0 mM EDTA), the fragments were again extracted with phenol, phenol/chloroform, and chloroform and precipitated with ethanol, resuspended in sterile TE, and microinjected into the male pronuclei by F2 hybrid eggs with C57B1/6× SJL parents as described by Brinster et al. (1985, Proc. Natl. Acad. Sci. 82:4438–4442).

7.1.3. DNA Analysis

Total nucleic acids were prepared from 16-day fetal liver and brain, as described previously (Brinster et al., 1985, supra). Samples that contained the injected constructs were determined by DNA dot hybridization of brain nucleic acids with human β-globin and HS II-specific probes that were labeled by extension of random primers (Feinberg and Vogelstein, 1983, Anal. Biochem. 132:6–13). The human β-globin probe was a 790-bp HinfI fragment from IVS 2, and the HS II probe was a 1.9-kb HindIII fragment spanning the HS II site. Hybridizations were performed at 68° C. for 16 hours in 5× SSC, 5× Denhardt's solution, 100 µg/ml herring sperm DNA, and 0.1% SDS. Filters were washed three times for 20 minutes each at 68° C. in 2× SSC, and 0.1% SDS and for 20 minutes at 68° C. in 0.2× SSC and 0.1% SDS (if necessary) to reduce background.

For Southern blots, 10 µg of fetal liver DNA from animals that were positive with HS II and/or β-globin probes were digested with BamHI and PstI, electrophoresed on 1.0% agarose gels, blotted onto nitrocellulose, and hybridized with the β and HS II probes described above. The hybridization conditions for Southern blots were the same as described for DNA dots.

7.1.4. RNA Analysis

RNA was prepared from total nucleic acids by digesting the sample with DNase I (Worthington, RNase-free) at 10 µg/ml for 20 minutes at 37° C. After digestion, RNA was purified by phenol/chloroform and chloroform extraction, precipitated with ethanol, and resuspended in TE.

Quantitation of human and mouse β-globin mRNA was determined by solution hybridization with oligonucleotide probes as described (Townes et al., 1985, EMBO J., 4:1715–1723). Primer extensions were performed as described by Townes et al. (1985, EMBO J., 4:1715–1723; 1985, Mol. Cell Biol. 5:1977–1983), except that only 5 μg of fetal liver or brain RNAs were analyzed and three oligonucleotides were used in each reaction. The human β primer 5'-AGACGGCAATGACGGGACACC-3' corresponds to sequences from +78 to +98 of the human β-globin gene. The mouse α primer 5'-CAGGCAGCCTTGATGTTGCTT-3' corresponds to sequences from −45 to −65 of the mouse α1- and α2-globin genes, which are identical in this region. The mouse β primer 5'-TGATGTCTGTTTCTGGGGTTGTG-3' corresponds to sequences +31 to +53 of the mouse $β^S$-globin gene. Although there are 2-bp differences in the $β^s$ and $β^t$ genes in the region covered by this oligonucleotide, comparison of solution hybridization results (obtained with a different oligonucleotide that is perfectly complimentary to $β^s$ and $β^t$-globin mRNA under the hybridization conditions used.

7.2. Results

7.2.1. Production of HSβ-Globin Transgenic Mice

FIG. 6 illustrates the seven constructs that were purified from vector sequences and injected into fertilized mouse eggs. These eggs were transferred into the uteri of pseudopregnant foster mothers, and the embryos were removed after 16 days of development. Total nucleic acids were prepared from the erythroid fetal livers and from brains, and transgenic mice were identified by DNA dot hybridization with β-globin and HS II-specific probes. Fetal liver DNA from positive animals was then analyzed by Southern blotting to determine transgene copy number and integrity. FIG. 7 illustrates the Southern blots used to determine transgene copy number. Lanes 1–3 of each blot are herring sperm DNA spiked with the equivalent of 50, 5.0, and 0.5 or 25, 2.5, and 0.25 copies per cell of the respective construct; lane 4 is human DNA; and lane 5 is a nontransgenic mouse control. The controls and fetal liver DNA from each sample were digested with BamHI and PstI, and blots were hybridized with a human β-globin IVS 2 probe. A single 1.7-kb band was observed in all of the samples except the negative controls. The intensity of this band was compared to the standards in lanes 1–4 to determine transgene copy number. The number of copies per cell of the transgene is listed in parenthesis after each sample number. These values ranged from 0.25 to 150 copies per cell. Mice that contained less than one copy per cell are probably mosaics that inegrated the transgene at the two- or four-cell stge. All of the samples were cut with several other enzymes and Southern blots were probed with various HS site and β-globin probes to determne transgene integrity. All of the animals contained intact constructs except for samples 5140 and 5153 of HS II (5.8) β. Although the human β-globin gene was intact, the HS II site in both of these samples was rearranged.

7.2.2. Expression of Human β-Globin mRNA in HS β-Transgenic Mice

Human and mouse β-globin mRNA levels were determined for each fetal liver and brain sample by solution hybridization with oligonucleotide probes as described previously (Townes et al., EMBO J. 4:1715–1723). In addition, fetal liver RNA was analyzed for correctly initiated human β-globin and mouse α- and β-globin mRNAs by primer extension. Mice switch directly from embryonic to adult hemoglobin synthesis when fetal liver becomes the major site of erythropoiesis at 13–17 days of development. Therefore, 16-day fetal liver is considered an adult erythroid tissue. FIG. 8 illustrates the primer extension gel of fetal liver RNA from HS I-VI β transgenic mice. The HS I-VI construct contains all five upstream and one downstream DNase I HS sites flanking the human β-globin gene (FIG. 6). Lane 1 is human reticulocyte RNA, and lane 2 is fetal liver RNA from a non-transgenic mouse control. The authentic human β-globin primer extension product is 98 bp, and the correct mouse α- and β-globin products are 65 and 53 bp, respectively. All three of the animals that contained the HS I-VI β transgene expressed correctly initiated human β-globin mRNA; and the levels of expression, which are listed in parentheses after each sample number, ranged from 5.0 to 26% of endogenous mouse β-globin mRNA. As there are four copies of the mouse β-globin gene per diploid genome ($2β^s$ and $2β^t$ alleles in the β single haplo-type mouse, (Weaver et al., 1981, Cell 24:403–411), the levels of human and mouse β-globin mRNAs were divided by their respective gene copy numbers to make a direct comparison of expression. The corrected values for human β-globin mRNA ranged from 20 to 84% of endogenous mouse β-globin mRNA, and the average level of expression was 52% per gene copy (Table II).

To determine whether the downstream HS VI site was required for high level β-globin gene expression, a construct containing only the five upstream HS sites (HS I-V (30) β; FIG. 6) was analyzed in transgenic mice. This construct contains the five HS sites on a 30-kb fragment linked upstream of the human β-globin gene. Thirteen animals that contained intact copies of the transgene were obtained, and all 13 expressed human β-globin mRNA in fetal liver. FIG. 9 illustrates the primer extension gel of fetal liver RNA from the HS I-V (3) β construct. Levels of human β-globin mRNA ranged from 18 to 316% of endogenous mouse β-globin mRNA. When these values were corrected for transgene copy number, the average level of expression per gene copy was 108% of endogenous mouse β-globin mRNA (Table II).

A construct that contained all five upstream HS sites on a smaller fragment (22 kb) was also assayed for activity. Nine animals containing intact copies of the HS I-V (22) β transgene (FIG. 6) were obtained, and all nine expressed human β-globin mRNA in fetal liver. Fetal liver RNA from eight of these samples was analyzed by primer extension. The results are illustrated in FIG. 10. All eight animals expressed correctly initiated human β-globin mRNA, and the levels of expression ranged from 52 to 380% of endogenous mouse β-globin mRNA. The lowest expressor (4854), which expressed human β-globin mRNA at 1.0% of the level of mouse β-globin mRNA, was not included on the gel. When the level of expression for all nine animals was corrected for transgene copy number, the average level of expression per gene copy was 109% of endogenous mouse β-globin mRNA (Table II).

To determine whether all five upstream HS sites are required for high level erythroid expression, a construct containing only HS I and HS II on a 13-kb MluI-ClaI fragment was inserted upstream of the human β-globin gene (FIG. 6) and tested for activity. Thirteen animals that contained intact copies of the HS I, II (13) β transgene were obtained, and all 13 animals expressed correctly initiated human β-globin mRNA in fetal liver (FIG. 11). Levels of expression ranged from 9.0 to 347% of endogenous mouse β-globin mRNA. When these values were corrected for transgene copy number, the average level of human β-globin expression was 49% of endogenous mouse β-globin expression (Table II).

The 13.0-kb MluI-ClaI fragment containing HS I and HS II was then divided into a 5.8-kb MluI-BstEII fragment containing HS II and a 7.2-kb BstEII-ClaI fragment containing HS I. Each of these fragments was inserted upstream of the human β-globin gene (FIG. 6) and injected into fertilized eggs. Unfortunately, no HS I β transgenic animals were obtained. However, nine animals containing the HS II (5.8) β construct were identified by DNA dot hybridization, and seven of these nine animals contailned intact copies of the transgene. Fetal liver RNA from all nine samples was analyzed by solution hybridization and primer extension, and eight of nine animals expressed correctly initiated human β-globin mRNA (FIG. 12). The single animal (5120) that did not express any human β-globin mRNA was the only one of 51 HS β transgenic animals that did not express the transgene. The levels of expression for samples 5140 and 5153 were low but, as described above, both of these samples contained rearranged copies of the transgene. Also, the fetal liver RNA of sample 5127 was somewhat degraded. The levels of β-globin mRNA for samples 5127, 5118, 5132, 5131, 5148, and 5136 ranged from 8.0 to 108% of endogenous mouse β-globin mRNA. When these levels were corrected for transgene copy number, the values ranged from 6.0 to 84%, and the average level of human β-globin mRNA per gene copy was 40% of endogenous mouse β-globin mRNA (Table II).

TABLE II

SUMMARY OF HS β TRANSGENE EXPRESSION

| Transgene | Fraction expressors | Percent Endogenous mouse β-globin mRNA | Percent expression per gene copy | |
|---|---|---|---|---|
| | | | mean | range |
| HS I-VIβ | 3/3 | 5–26 | 52 | 20–84 |
| HS I-V (30) β | 13/13 | 18–316 | 108 | 16–200 |
| HS I-V (22) β | 9/9 | 1–380 | 109 | 2–208 |
| HS I, II (13) β | 13/13 | 9–347 | 49 | 9–92 |
| HS III (5.8) β | 6/7 | 8–108 | 40 | 6–84 |
| HS II (1.9) β | 4/4 | 56–194 | 40 | 13–63 |
| β | 7/23 | 0.2–23 | 0.3 | 0.1–0.6 |

Human and mouse β-globin mRNA levels were quantitated by solution hydribidzation with human β- and mouse β-globin-specific oligonucleotides, as described in the text. The values of percent expression per gene copy were calculated assuming four mouse β-globin genes per cell. Mice used in this study (C578L/6× SJL) F2 have the Hbb$^s$ or single haplotype. The β-globin locus in this halotype contains two adult β-globin genes (β$^s$ and β$^t$ per haploid genome (Weaver et al., 1981, Cell 24:403–411). The mice also have two α-globin genes α1 and α2 per haploid genome (Whitney et al. 1981, Proc. Natl. Acad. Sci. U.S.A. 78:7644–7647 Erhart et al. 1987, Genetics 115:511–519). Copies per cell of HS β transgenes were determined by densitometric scanning of the Southern blots illustrated in FIG. 7.

$$a \frac{h\beta\, mRNA}{m\beta\, mRNA} \times 100$$

$$b \frac{h\beta\, mRNA \,/\, h\beta\, \text{gene}}{m\beta\, mRNA \,/\, m\beta\, \text{gene}} \times 100$$

To begin to determine the terminal HS II sequence required for high level expression, a 1.9-kb KpnI-PvuII fragment containing HS III was inserted upstream of the human -globin gene (FIG. 6) and tested for activity in transgenic mice. Four animals that contained intact copies of the transgene were obtained and all four expressed correctly initiated human β-globin mRNA in fetal liver (FIG. 13). The levels of human β-globin mRNA ranged from 56 to 194% of endogenous mouse β-globin mRNA. When these values were corrected for transgene copy number, the average level of human β-globin mRNA was 40% of endogenous mouse β-globin mRNA (Table II).

Finally, the human β-globin gene without HS sites was injected into fertilized eggs and assayed for expression in 16-day fetal liver. In this experiment, only 7 of 23 mice that contained intact copies of the transgene expressed human β-globin mRNA, and the levels of expression ranged from 0.2 to 23% of endogenous mouse β-globin mRNA. When these levels were corrected for transgene copy number, the average level of human β-globin mRNA was 0.3% of endogenous mouse β-globin mRNA (Table II).

7.2.3. Tissue Specificity of HS β-Globin Transgene Expression

Fetal liver and brain RNA from the highest expressor or each set of transgenic animals were analyzed for human β, mouse α- and mouse β-globin mRNA by primer extension to assess the tissue specificity of human β-globin gene expression. Data in FIG. 10 and in the last two lanes of FIG. 13 demonstrate that the human β-globin gene is expressed in fetal liver and not in brain. The small amount of human β-globin mRNA in the brain results from blood contamination because equivalent amounts of mouse α- and β-globin mRNA are also observed in this nonerythroid tissue. Solution hybridization analysis demonstrated that the ratio of human β-globin mRNA to mouse β-globin mRNA was virtually identical in fetal liver and brain in all 50 HS β-transgenic mice. These data strongly suggest that the HS sites act specifically in erythroid tissue to stimulate high levels of human β-globin gene expression in transgenic mice.

7.3. Discussion

7.3.1. Summary of HB β-Globin Expression

A summary of the results presented above are listed in Table II. In this study only 7 of 23 animals without HS sites expressed the transgene. In contrast, 50 of 51 animals that contained HS sites inserted upstream of the human β-globin gene expressed correctly initiated human β-globin mRNA in fetal liver and no expression was detected in fetal brain. These results, like those of Grosveld et al. (1987 Cell 51:75–85) with a construct containing HS I-VI β, suggest that the HS sites activate expression regardless of the site of transgene integration. However, expression is not totally position independent. The range of expression varied widely with all of the constructs tested, and levels of human β-globin mRNA were not absolutely correlated with transgene copy number. Nevertheless, the average levels of expression per gene copy were high for all of the HS β-globin constructs tested. The HS I-V (30) β and HS I-V (22) β constructs were expressed at an average level of 108 and 109%, respectively, of endogenous mouse β-globin per gene copy, and all other HS-β-constructs were expressed at 40–49% of endogenous mouse β-globin per gene copy. This high level of expression was obtained even when a 1.9-kb fragment containing only HS II was inserted upstream of the human β-globin gene. The average level of expression per gene copy for a human β-globin construct that did not contain HS sites was only 0.3% of endogenous mouse β-globin. This average level of expression is 133–363 times lower than constructs containing HS sites. Finally, we suspect that the average level of expression for the HS I-VI β construct was lower than 100% per gene copy because only three animals were obtained.

7.3.2. Role of Individual Hypersensitivity Sites

Southern blots of fetal liver DNA from all 51 of the HS β- transgenic mice generated in this study demonstrated head-to-tail tandem arrays of the transgene. Therefore, every animal contains at least one copy of the human β-globin gene that is flanked on either side by HS sites. This is true even for animals that contain one or fewer copies per cell of the transgene. These animals must be mosaics (Wilke et al. 1986 Dev. Biol. 118:9–18) with multiple tandemly linked transgenes in only a fraction of their cells. Although the data demonstrate that HS VI is not required for high level expression, a copy of HS II or one of the other upstream HS sites may substitute for HS VI when inserted downstream of the β-globin gene in the tandem array. To determine whether a downstream HS site is required for high level expression, animals containing a single copy of HSI-V β or HS II β will have to be produced.

We have not yet tested the activity of HS III, HS IV, or HS V, inserted individually upstream of the human β-globin gene. However, one or more of these sites may be active because transgenic animals, that contain HS I-V consistently express higher levels of human β-globin mRNA than animals than contain HS I and HS II or HS II alone.

Because HS I β transgenic animals were not obtained, we do not know whether HS I alone can stimulate β-globin gene expression. However, two pieces of data argue strongly that HS I is not sufficient to enhance expression. First, we have demonstrated recently that the human α-globin gene is expressed at high levels in transgenic mice when placed downstream of HS I and HS II. Of 12 HSI, HSII, β-globin mice, 11 expressed correctly initiated human α-globin mRNA specifically in erythroid tissue, and the average percent expression per gene copy was 57% of endogenous mouse β-globin mRNA. The single animal that did not express human α-globin mRNA had intact copies of HS I α-globin, but the HS II site had been deleted upon integration. This result suggests that HS I alone cannot enhance expression. Second, a very interesting deletion in a Hispanic β-thalassemic patient has recently been defined by C. Driscoll et al. A 30-kb deletion that ends 9.8 kb upstream of the E-globin gene moves HS V-II but leaves HS I intact (FIG. 5). The patient, who has a $\beta^S$ gene on this same chromosome, makes no sickle hemoglobin. The data from this patient and the transgenic animal described above strongly suggest that HS I cannot, by itself, stimulate expression of downstream globin genes.

7.3.3. HS Site Effect on Other Genes

The effects of erythroid specific HS sites on other tissue specifically expressed genes has not been tested. However, the experiments of Nandi et al. (1988, Proc. Natl. Acad. sci. U.S.A. 85:3845–3849) strongly suggest that the SV40 promoter can be dramatically influenced by HS sites. Murine erythroleukemia (MEL) cells containing human chromosome 11 were transfected with a construct containing a modified human β-globin gene and an SVneo gene. G418 resistant cells were identified that contained this construct inserted specifically into the human β-globin locus or at nonspecific chromosomal sites. When these cells were induced to differentiate with dimethylsulfoxide (DMSO), Svneo mRNA was induced to high levels in cells with site-specific integrants but not in cells with random integrants. These results strongly suggest that expression from heterologous promoters can be greatly enhanced by the HS sites. We have also demonstrated that SVneo expression is induced to high levels in MEL cells transfected with cosmids containing HS I-V β linked to the SVneo gene.

7.3.4. Human β-Globin Domain

Several groups have suggested that HS sites mark the boundaries of the human β-globin domain and that these sites are responsible for opening the β-globin domain specifically in erythroid tissue (Tuan et al., 1985, Proc. Natl. Acad. Sci. U.S.A. 82:6384–6388; Grosveld et al., 1987, Cell 51:75–85). Forrester et al. (1987 Nucl. Acids Res. 15:10159–10177) have demonstrated recently that three HS sites are formed in human fibroblasts that have been fused with MEL cells. These hybrids synthesize high levels of human β-globin mRNA. Presumably, trans-acting factors present in MEL cells interact downstream of the human β-globin locus and organize the previously closed chromatin domain into an open domain. Therefore, Forrester et al. (1987, supra) have suggested that the sequences be called locus activating regions, or LARs. Similarly, in the developing human embryo, trans-acting factors present in early erythroid cells may interact with hypersensitive site sequences and activate the β-globin locus for expression.

7.3.5. Model For Developmental Regulation

Choi and Engel (1988, Cell 55:17–26) have demonstrated recently that sequences at the immediate 5' end of the chicken β-globin gene are involved in temporal specificity in transient expression assays. These sequences apparently bind factors that influence the ability of this promoter to compete with the α-globin gene promoter for interactions with a single erythroid enhancer (Choi and Engel, 1988, supra; Nickol and Feisenfeld, 1988 Proc. Natl. Acad. Sci. 85:2548–2552) located in the chicken β-globin locus. Although similar mechanisms may be involved in developmental stage-specific expression of human globin genes, the situation is probably more complex. The major determinants of erythroid tissue specificity in humans appear to be the HS sequences. In fact, these sequences carry out two important functions. They organize the entire β-globin locus for expression specifically in erythroid tissue, and they act as an enhancer to direct high level expression. These two separate but related functions are evident in the experiments described above. First, the HS sites increase the fraction of transgenic animals that express the human β-globin gene. Of 51 HS β-globin mice, 50 expressed the transgene specifically in erythroid tissue compared with 7 of 23 animals containing that β-globin gene alone. Apparently, the HS sequences ensure that the transgene will be in an open chromatin domain regardless of the site of integration. Second, HS sites stimulated the average level of β-globin gene expression 133- to 363-fold compared to the average level of the β-globin gene alone. Therefore, these sequences constitute a powerful enhancer that may work in concert with enhancers in and surrounding individual genes.

Although human β-globin genes in transgenic mice are expressed specifically in adult erythroid tissue without HS sites, high levels of correctly regulated expression may require interactions between HS sequences, promoters, and proximal enhancers. A model for globin gene regulation can be envisioned that incorporates the two important functions of HS sites and the concept of competition between various regulatory sequences. HS sequences could be activated in early erythroid cell precursors and organize the entire β-globin locus into an open chromatin domain that is stable throughout development. Within the open domain, promoters and enhancers in and surrounding the ε, γ, and β-globin genes could then compete for interactions with the HS master enhancer to determine which of these genes will be expressed. Promoter and proximal enhancer binding factors synthesized in yolk sac, fetal liver, and bone marrow could influence these competitive interactions either positively or negatively and subsequently determine developmental specificity. Transgenic mouse experiments with constructs containing human ε, γ, and β-globin genes inserted separately or in various combinations downstream of the HS sites should help define important interactions between regulatory sequences and should, in general, provide meaningful insights into the complex mechanisms that regulate multigene families during development. See also Ryan et al., 1989, Genes and Dev. 3:314–323, which is incorporated by reference in its entirety.

8. EXAMPLE

Synthesis of Functional Human Hemoglobin In Transgenic Mice

8.1. Materials and Methods

8.1.1. α and β-Globin Gene Constructs

A 12.9-kb MluI-ClaI fragment that contained erythroid specific, DNase I super-hypersensitive (HS, arrow, FIG. 15) sites I and II from the human β-globin locus was inserted into a modified pUC19 plasmid upstream of a 3.8-kb Bg/lII-EcoRI fragment carrying the human α1-globin gene or a 4.1-kb HpaI-XbaI fragment with the human β-globin gene.

8.1.2. Generation of Transgenic Animals

The 16.7 and 17.0 kb fragments with HS I, II α-globin and HS I, II β-globin were separated from plasmid sequences and coinjected into fertilized mouse eggs as described by Brinster et al. (1985, Proc. Natl. Acad. Sci. U.S.A. 82: 4438–4442).

8.2. Results

8.2.1. Tissue-Specific Expression of αND β-Globin Transgenes

HS I and II (a 12.9-kb Mlu-I-Cla I fragment) were inserted upstream of the human α1- and β-globin genes (FIG. 15 and equimolar amounts of these constructs were coinjected into fertilized mouse eggs (Brinster et al., 1985, Proc. Natl. Acad. Sci. U.S.A. 82:4438). The eggs were transferred into the oviducts of pseudopregnant foster mothers, and seven transgenic mouse lines were established from founder animals that contained intact copies of the injected fragments. Total RNA from ten tissues of adult progeny were then analyzed for correctly initiated human α-, human β-, mouse α-, and mouse β-globin mRNA by primer extension (Townes et al., 1985, Mol. Cell. Biol. 5:1977–1983; Townes et al., 1985, EMBO J. 4:1715–1723). Human α- and β-globin trangenes were expressed only in blood and spleen, which are body erythroid tissues in mice; detection in the lung is the result of blood contamination because both human and mouse α- and β-globin mRNA are observed in this nonerythroid tissue. Human α- and β-globin mRNA levels in blood, as measured by solution hybridization, were 100% and 120% of endogenous mouse β-globin mRNA, respectively. Therefore, erythroid-specific, human α- and β-globin gene expression can be achieved in adult transgenic mice after coinjection of α- and β-globin constructs that contain HS I and II.

8.2.2. Identification of Human Hemoglobin In Transgenic Mice

Figure 16C:
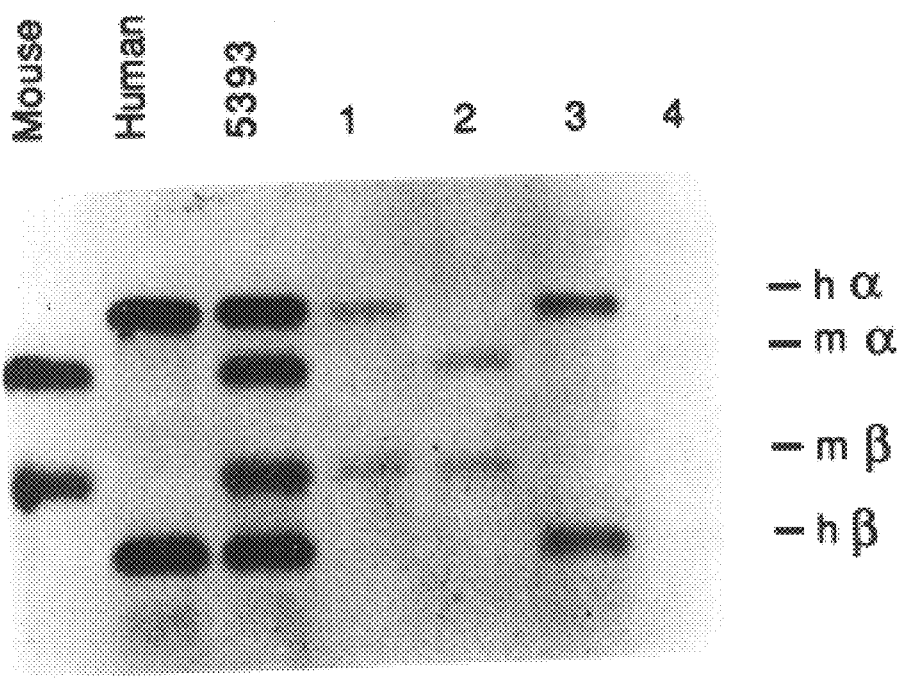

To determine whether complete human hemoglobins were formed, we separated hemolysates of the blood of animals from two different transgenic lines by non-denaturing isoelectric focusing (IEF) (FIG. 14B). The first lane is a mouse control and the last lane is a normal human sample. The predominant band in each of the controls is the major adult hemoglobin, mouse $α_2β_2$ or human $α_2β_2$, respectively. In both transgenic mouse samples 5394 and 5393, bands that run at the same pI as human Hb A ($hα_2h_{β2}$ and mouse hemoglobin ($mα_2mβ_2$) were observed. In addition to human and mouse hemoglobins, two other major bands were observed in both transgenic samples. To determine the composition of these bands and to confirm the human and mouse hemoglobins, the four bands in sample 5393 were excised from the gel and analyzed on a denaturing cellulose acetate strip (FIG. 16C) Control lysates of mouse, human, and 5393 blood samples were separated in lanes on the left. Mouse α- and β-globin polypeptides, as well as human α- and β-globin polypeptides, were well separated on this strip. Sample 5393 contained all four polypeptides, the human α- and β-globin polypeptides were 110% and 106% of the amounts of mouse α- and β-globin, by densitometric analysis. The top band (band 1) of sample 5393 in FIG. 16B is composed of human α- and mouse β-globin chains. The second band is mouse α- and mouse β-globin and the third band is human α and β-globin as expected. The polypeptides composing band 4 in FIG. 16B are barely visible in FIG. 16C but are clearly mouse α- and human β-globin. Therefore, normal amounts of human hemoglobin can be synthesized in adult mice, and multiple combinations of globin polypeptides are possible.

8.2.3. Functional Properties of Human Hemoglobin In Transgenic Mice

The functional properties of human, mouse, and hybrid hemoglobins synthesized by transgenic mice were assessed by determination of oxygen equilibrium curves (OEC) and by calculation of $P_{50}$ values. The $P_{50}$ is the partial pressure at which hemoglobin is half saturated with oxygen and is inversely related to hemoglobin oxygen affinity. All four hemoglobins described above were purified by preparative isoelectrophoresis and the OEC for each was determined. The OEC were normal, sigmoid-shaped, and demonstrate that all four hemoglobins bind oxygen cooperatively. The $P_{50}$ of human hemoglobin synthesized by transgenic mice is 8.0 mmHg, which is identical to the $P_{50}$ of native human Hb A. Interestingly, the oxygen affinities of the two hybrid tetramers differ significantly from human and mouse hemoglobins. The $h\alpha_2m\beta_2$ hybrid was observed to have an extremely low $O_2$ affinity; the $P_{50}$ was 15.7 mmHg. In contrast, the $O_2$ affinity for $m\alpha_2h\beta_2$ was extremely high; the $P_{50}$ for this hemoglobin was 4.7 mmHg.

Finally, the hematological values of six transgenic progeny were determined, and compared to five normal animals. Red blood cell counts and hematocrits for transgenic animals were normal and interestingly, the values for hemoglobin and mean corpuscular volume were in the normal range. Consequently, the calculated values of mean corpuscular hemoglobin and mean corpuscular hemoglobin concentration (MCHC) for transgenic animals were normal. Thus, the total hemoglobin concentration in transgenic erythrocytes is not increased even though reticulocytes contain 100% more globin mRNA. Therefore, to maintain normal MCHC, all globin mRNAs are either translated at reduced rates or $\alpha$ and $\beta$-globin polypeptides are less stable. Another possibility is that globin synthesis ceases when the maximum intracellular concentration of hemoglobin is attained. If the rate of globin synthesis is normal, then a full complement of hemoglobin could be synthesized in half the time leading to faster maturation of reticulocytes.

8.3. Discussion

In summary, the results presented demonstrate that high levels of human $\alpha$- and $\beta$-globin mRNA can be coexpressed in mice. The transgenes are expressed specifically in erythroid tissue and levels of human hemoglobin equivalent to mouse hemoglobin can be achieved. In addition, the human hemoglobin produced in these mice is fully functional and the transgenic animals are phenotypically normal. These results provide a solid foundation for the production of transgenic mice that synthesize high levels of other human hemoglobins. See also Behringer et al., 1989, Science 245:971–973, which is incorporated by reference in its entirety herein.

9. EXAMPLE

Expression of Human Sickle Hemoglobin In Transgenic Mice

9.1. Materials and Methods

9.1.1. DNA Constructs

The human globin constructs included hypersensitivity regions I-V in conjunction with human $\alpha$ globin (cosmids HSI-V $\alpha$) and human $\beta^S$-globin (HSI-V $\beta^S$).

9.1.2. Sample Preparation and Microinjection

The constructs were removed from vector sequences by digestion with the appropriate enzymes and isolated in low-gelling temperature agarose (FMC) gels. Gel slices were melted, extracted twice with buffered phenol, once with phenol/chloroform, and once with chloroform and precipitated with ethanol. After suspension in TE (10 mM Tris-HCl (pH 8.0), 1.0 mM EDTA), the fragments were again extracted with phenol, phenol/chloroform, and chloroform and precipitated with ethanol. The purified fragments were washed with 70% ethanol, resuspended in sterile TE, and microinjected into the male pronuclei of F2 hybrid eggs from C57BL/6XSJL parents as described by Brinster et al. (1985, Proc. Natl. Acad. Sci. U.S.A. 82:4438–4442).

9.2. Results and Dicussion

Blood samples were obtained from transgenic mice carrying the human $\alpha$ and $\beta^S$ constructs. When the partial pressure of oxygen was decreased in vitro, the transgenic mouse red blood cells were observed to sickle in a manner comparable to that exhibited by red blood cells from a patient suffering from sickle cell anemia (FIG. 18; FIG. 21). Although the classic phenotype is a sickled cell, the most common cells even in homozygous patients are elongated, rigid cells resulting from polymerization of sickle hemoglobin chains under low oxygen tension. Such polymerization is illustrated in FIG. 21C.

10. EXAMPLE

Expression of LAC Z In Erythroid Cells of Transgenic Mice

Plasmid pTR159 was constructed as follows. The HSII$\beta$ plasmid was digested with NcoI and Bam HI, and the DNA fragment containing the first exon, second intron, and part of the second exon was removed. This sequence was replaced with an NcoI-BglII DNA fragment containing the lac Z gene. A fragment of DNA that contained HSII $\beta$/lac Z/$\beta$ was purified from vector sequences and injected into fertilized mouse eggs as outlined supra.

Several animals that contained intact copies of the transgene were identified by Southern blot analysis of genomic DNA, and were mated to control animals in order to establish lines.

FIG. 20 is a picture of erythroid cells that have been incubated with the chromogenic substrate X-GAL. A blue color results when the enzyme (lac Z) cleaves the substrate (arrow points to blue cell). This experiment proves that foreign proteins other than globin may be synthesized at high levels in transgenic erythrocytes and provides the foundation for production of many other biologically important proteins in this system. 11. Deposit of Cosmid DNAS The following recombinant cosmid DNA were deposited with the American Type Culture Collection in Rockville, Md.

| cosmid | HS I-V-$\alpha$ |
| cosmid | HS I-V-$\beta$ |
| cosmid | HS I-V-$\beta^S$ |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A recombinant nucleic acid vector for expressing a gene encoding a protein of interest in an erythroid cell, comprising, in operable association,
   DNase I hypersensitive sites I and II of a mammalian $\beta$-globin gene, a promoter, and a gene encoding a protein of interest, wherein said DNase I hypersensitive sites and said promoter direct expression of said gene in said erythroid cell, and wherein said vector does not comprise any of DNase I hypersensitive sites III, IV, V, and VI of a mammalian $\beta$-globin gene.

2. The recombinant nucleic acid vector of claim 1, wherein said vector is a plasmid.

3. The recombinant nucleic acid vector of claim 1, wherein said vector is a cosmid.

4. The recombinant nucleic acid vector of claim 1, wherein said vector is a bacteriophage.

5. The recombinant nucleic acid vector of claim 1, wherein said vector is a virus.

6. The recombinant nucleic acid vector of claim 5, wherein said virus is a retrovirus.

7. The recombinant nucleic acid vector of claim 1, wherein said protein of interest is a globin.

8. The recombinant nucleic acid vector of claim 7, wherein said globin is an α-globin.

9. The recombinant nucleic acid vector of claim 7, wherein said globin is a β-globin.

10. The recombinant nucleic acid vector of claim 1, wherein said promoter is a non-β-globin promoter.

11. A recombinant nucleic acid vector for expressing a gene encoding a protein of interest in an erythroid cell, comprising, in operable association, DNase I hypersensitive site II of a mammalian β-globin gene, a promoter, and a gene encoding a protein of interest, wherein said DNase I hypersensitive site and said promoter direct expression of said gene in said erythroid cell, and wherein said vector does not comprise any of DNase I hypersensitive sites I, III, IV, V, and VI of a mammalian β-globin gene.

12. The recombinant nucleic acid vector of claim 11, wherein said vector is a plasmid.

13. The recombinant nucleic acid vector of claim 11, wherein said vector is a cosmid.

14. The recombinant nucleic acid vector of claim 11, wherein said vector is a bacteriophage.

15. The recombinant nucleic acid vector of claim 11, wherein said vector is a virus.

16. The recombinant nucleic acid vector of claim 15, wherein said virus is a retrovirus.

17. The recombinant nucleic acid vector of claim 11, wherein said protein of interest is a globin.

18. The recombinant nucleic acid vector of claim 17, wherein said globin is an α-globin.

19. The recombinant nucleic acid vector of claim 17, wherein said globin is a β-globin.

20. The recombinant nucleic acid vector of claim 11, wherein said promoter is a non-β-globin promoter.

21. A recombinant nucleic acid vector for expressing a gene encoding a protein of interest in an erythroid cell, comprising, in operable association, at least one mammalian β-globin DNase I hypersensitive site selected from the group consisting of DNase I hypersensitive site I, II, III, IV, V, VI, and a combination thereof, an α-globin promoter, and a gene encoding a protein of interest, wherein said at least one DNase I hypersensitive site and said promoter direct expression of said gene in said erythroid cell.

22. The recombinant nucleic acid vector of claim 21, wherein said vector comprises mammalian β-globin DNase I hypersensitive site II.

23. The recombinant nucleic acid vector of claim 22, wherein said vector further comprises mammalian β-globin DNase I hypersensitive site I.

24. The recombinant nucleic acid vector of claim 21, wherein said vector comprises mammalian β-globin DNase I hypersensitive sites I, II, III, IV, and V.

25. The recombinant nucleic acid vector of claim 24, wherein said vector further comprises β-globin DNase I hypersensitive site VI.

26. The recombinant nucleic acid vector of claim 21, wherein said protein of interest is a globin.

27. The recombinant nucleic acid vector of claim 26, wherein said globin is an α-globin.

28. The recombinant nucleic acid vector of claim 26, wherein said globin is a β-globin.

29. The recombinant nucleic acid vector of claim 21, wherein said vector is a plasmid.

30. The recombinant nucleic acid vector of claim 21, wherein said vector is a cosmid.

31. The recombinant nucleic acid vector of claim 21, wherein said vector is a bacteriophage.

32. The recombinant nucleic acid vector of claim 21, wherein said vector is a virus.

33. The recombinant nucleic acid vector of claim 32, wherein said virus is a retrovirus.

* * * * *